United States Patent
Witcomb et al.

(10) Patent No.: US 10,588,702 B2
(45) Date of Patent: Mar. 17, 2020

(54) SYSTEM AND METHODS FOR UPDATING PATIENT REGISTRATION DURING SURFACE TRACE ACQUISITION

(71) Applicant: SYNAPTIVE MEDICAL INC., Toronto (CA)

(72) Inventors: Neil Jeffrey Witcomb, Toronto (CA); Sepide Movaghati, Toronto (CA); Adam Taylor Scott, Toronto (CA)

(*) Notice: Subject to any disclaimer, the term of this patent is extended or adjusted under 35 U.S.C. 154(b) by 0 days.

(21) Appl. No.: 16/510,867

(22) Filed: Jul. 12, 2019

(65) Prior Publication Data
US 2019/0336225 A1 Nov. 7, 2019

Related U.S. Application Data

(63) Continuation of application No. 16/118,635, filed on Aug. 31, 2018, now Pat. No. 10,390,892, which is a continuation-in-part of application No. 15/553,426, filed as application No. PCT/CA2016/050506 on May 2, 2016, now Pat. No. 10,111,717.

(51) Int. Cl.

| | |
|---|---|
| *G06K 9/00* | (2006.01) |
| *A61B 34/20* | (2016.01) |
| *G16H 10/60* | (2018.01) |
| *A61B 34/10* | (2016.01) |
| *G06T 7/30* | (2017.01) |
| *A61B 5/107* | (2006.01) |
| *A61B 5/055* | (2006.01) |

(52) U.S. Cl.
CPC ............ *A61B 34/20* (2016.02); *A61B 5/1077* (2013.01); *A61B 34/10* (2016.02); *G06T 7/30* (2017.01); *G16H 10/60* (2018.01); *A61B 5/055* (2013.01); *A61B 2034/101* (2016.02); *A61B 2034/2068* (2016.02); *A61B 2034/2074* (2016.02)

(58) Field of Classification Search
None
See application file for complete search history.

(56) References Cited

U.S. PATENT DOCUMENTS

| | | | |
|---|---|---|---|
| 5,672,885 | A | 9/1997 | Allen et al. |
| 7,398,116 | B2 | 7/2008 | Edwards |
| 7,438,931 | B2 | 10/2008 | Brewer et al. |
| 7,751,868 | B2 | 7/2010 | Glossop |
| 9,241,657 | B2 | 1/2016 | Vollmer et al. |

(Continued)

*Primary Examiner* — Hadi Akhavannik
(74) *Attorney, Agent, or Firm* — Thanh V. Vuong

(57) ABSTRACT

A surgical navigation system and method for identifying positions on a patient, including a processor, and a tracking system for tracking a pointer tool. The processor is programmed to initialize a surface trace acquisition, continuously record the positions of the pointer tool during the surface, conduct trace acquisition, combine the positions recorded during the surface trace acquisition into a surface trace, receive a patient image of the patient, extract a surface from the patient image, compute a registration transform between the surface traces and the surface for patient registration, segment the patient image into a regions where each region contains an anatomical landmark, determine a spatial distribution of surface traces among the regions; determine whether the spatial distribution in relation to each region minimizes deviance below a threshold, and if the determination is exceeding the threshold, provide information relating to such region.

8 Claims, 21 Drawing Sheets

(56) References Cited

U.S. PATENT DOCUMENTS

| | | |
|---|---|---|
| 2004/0172198 A1 | 9/2004 | Talaalout et al. |
| 2006/0004284 A1* | 1/2006 | Grunschlager .......... A61B 6/00 |
| | | 600/416 |
| 2007/0060799 A1 | 3/2007 | Lyon et al. |
| 2014/0176561 A1 | 6/2014 | Nakamura |
| 2014/0193053 A1 | 7/2014 | Kadoury et al. |
| 2016/0015471 A1 | 1/2016 | Piron et al. |
| 2016/0070436 A1* | 3/2016 | Thomas ................ A61B 5/055 |
| | | 715/771 |

* cited by examiner

SYSTEM AND METHODS FOR UPDATING PATIENT REGISTRATION DURING SURFACE TRACE ACQUISITION

CROSS-REFERENCE TO RELATED APPLICATION(S)

This application is a continuation from U.S. application Ser. No. 16/118,635, filed on Aug. 31, 2018, entitled "System and Methods for Updating Patient Registration During Surface Trace Acquisition". This application also claims the benefit of, and priority to, U.S. patent application Ser. No. 15/553,426, filed on Aug. 24, 2017, entitled "System and Methods for Improving Patient Registration," in turn, claiming the benefit of, and priority to, PCT Patent Application Serial No. PCT/CA2016/050506, filed on May 2, 2016, entitled "Methods for Improving Patient Registration," all of which are herein, and hereby, incorporated by reference in their entirety.

TECHNICAL FIELD

The present disclosure generally relates to neurosurgical or medical procedures. More specifically, the present disclosure technically relates to systems and methods for improving the surface trace patient registration process by using a medical navigation system. Even more specifically, the present disclosure technically relates to systems and methods for updating patient registration by using a medical navigation system.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

During a medical procedure, navigation systems require a registration process to transform between the physical position of the patient in the operating room and the volumetric image set (e.g., MRI/CT) being used as a reference to assist in accessing the target area in the patient. Conventionally, this registration is done relative to the position of a patient reference, which is visible by the tracking system and stays fixed in position and orientation relative to the patient throughout the procedure.

This registration is typically accomplished through a touch-point registration method which involves constructing a correspondence of identifiable points (e.g., either fiducial or anatomic points) between the patient in the operating room and the volumetric image set of the patient. Such an approach to registration has a number of disadvantages, such as those that increase effort on the parts of the surgical team including requiring fiducials to be placed before patient scans, requiring points to be identified one at a time, requiring points to be reacquired. Additionally disadvantages of this method also affect the accuracy of the guidance system, such as providing for a limited number of points, touch point collection is subject to user variability, and the physical stylus used for collecting the points can deform or deflect patient skin position, in addition the patient is required to be imaged directly before the procedure and the fiducials may move/fall off.

Another approach to performing a registration is the surface trace registration method which involves acquiring a contour of the patient, by drawing a line over the surface of the patient, usually acquiring a series of points, using either a tracked stylus pointer or a laser pointer and fitting that contour to the corresponding extracted surface from an image of the patient. In such related art methods, the surgeon must finish tracing and then wait approximately 30 seconds, depending on the number of points collected, before the surgeon can even view and verify the result of the registration. If the accuracy of the registration is not satisfying, the surgeon must add more traces or reperform the tracing and wait for the related art software to recalculate the registration. Moreover, the surgeon is informed of the number of collected points during tracing; however, no real-time information regarding the quality of the collected points is provided.

A related art example of registration challenges is experienced by the Brainlab® Softouch® system which collects registration points via touching specialized pointer to the skin, wherein registration points are collected one at a time. However, the Brainlab® Softouch® system does not provide real-time feedback relating to the quality of the registration points being collected. Rather, the Brainlab® Softouch® system merely provides the number of points being collected, wherein the number of registration points being collected is a sparse collection of registration points.

Another related art example of registration challenges is experienced by the Brainlab® Z-Touch® system which collects registration points via a laser light incident on a patient's face, wherein registration points are continuously collected as the incident laser light traverses the patient's face, and wherein feedback is not improved over that of the Brainlab® Softouch® system.

Yet another related art example of registration challenges is experienced by the Medtronic® trace system which collects registration points via tracing a patient's face and skull with a pointer, wherein the registration points are continuously collected as the tool moves traverses the patient's face and skull. However, the Medtronic® trace system does not provide real-time feedback about the quality of the registration points, but merely provides an initial guess of their relative positions.

Therefore, a need exists in the related art for a real time, or nearly real time, feedback mechanism to better guide the surgeon through tracing as well as to improve the work flow time.

SUMMARY

The present disclosure addresses many challenges in the related art, such as inaccurate or delayed registration, in a system and methods for updating a patient registration during a surface trace acquisition, whereby real time registration refinement is provided, whereby a real time, or nearly real time, feedback mechanism to better guide the surgeon through tracing is provide, and whereby work flow time is decreased. The system and methods for updating a patient registration during a surface trace acquisition involve using a coverage metric based on anatomy rather than the number of points and using a non-linear template matching algorithm for initial registration, in accordance with embodiments of the present disclosure. The real-time tracing feedback allows the surgeon to refine their tracing without performing a lengthy registration first. The system and methods of the present disclosure are also configured to provide feedback if the collected points occur at a lower frequency than expected which could otherwise cause a worse registration than expected, given the appearance, to use a coverage metric based on a patient's anatomy, rather than exclusively based on the registration points, and to use a non-linear template-matching-based registration technique, rather than merely using a linear registration, for commencing registration.

In general, the present disclosure involves a computer implemented method for performing a patient registration using a processor of a surgical navigation system in a medical procedure, comprising the steps of initializing a surface trace acquisition, recording one or more surface traces, terminating the surface trace acquisition, receiving a patient image of a patient anatomy, extracting a surface from the patient image, and computing a registration transform for patient registration between the one or more surface traces and the patient image extracted surface. This method may also comprise computing the registration transform by minimizing a set of Euclidean distances. In some embodiments the step of computing a registration transform may comprise iteratively inputting registration transforms into a cost minimization function. In other embodiments the set of Euclidean distances used to compute the patient registration transform may include at least the distances between the surface traces and the extracted surface. In addition the method may comprise the steps of: initializing a fiducial position acquisition, recording the positions of fiducials on the patient, and receiving the location of fiducials points in the patient image. In other instances the set of Euclidean distances may include at least the distances between the surface traces and the extracted surface and the distances between the fiducials and the fiducial points.

In yet further embodiments the method may include the steps of: monitoring the position of a pointer tool, analyzing the position to determine if the pointer tool is motionless, and upon determining that the pointer tool is motionless for a predetermined amount of time prompting the surgical navigation system to initialize or terminate the surface trace. Furthermore the method may also comprise the steps of: receiving input from a user ranking the one or more surface traces, computing a weighting for the surface traces based on the ranking, applying the weighting to the surface traces, and computing the registration transform that minimizes a set of Euclidean distances between the one or more surface traces and the surface. In yet further embodiments the methods may further comprise: receiving input from a user of one or more regions of one or more surface traces to be culled, discarding the one or more regions from the one or more surface traces, and computing a registration transform that minimizes a set of Euclidean distances between the one or more surface traces and the surface after the regions have been discarded.

In some instances the method may also comprise the steps of: segmenting the patient image into regions, determining the spatial distribution of surface traces amongst the regions, determining whether the spatial distribution in each region minimize deviance below a threshold, and upon determining the spatial distribution in a region is above the threshold informing the user of the regions. It should be noted that the step of segmenting the patient image into regions, may further entail doing so such that each region contains an anatomical landmark such as the naison, the temples, the ears, the tip of the nose, the bridge of the nose, the shelves over the eyes, and etc. In some alternate instances the method may also comprise: initializing one or more landmark acquisitions, recording the positions of one or more landmarks on a patient, receiving the position of one or more landmark points in the patient image, and computing an initial registration transform that minimizes a set of Euclidean distances between the one or more landmarks and the one or more landmark points. The method as disclosed herein may also comprise using the initial registration transform to visualize an initial alignment of the patient's position with the patient image in an image space as well as visualizing the surface traces in the image space and this resultantly may assist the user in acquiring the surface traces.

Also generally disclosed in this application is a surgical navigation system used for navigated surgical procedures generally comprising: a tracked pointer tool for identifying positions on the patient, a tracking system for tracking the pointer tool, and a processor programmed with instruction to: initialize a surface trace acquisition, continuously record the positions of the pointer tool during the surface; trace acquisition, combine the positions recorded during the surface trace acquisition into a surface trace, terminate the surface trace acquisition, receive a patient image of the patient, extract a surface from the patient image, and compute a registration transform between the one or more surface traces and the surface for patient registration. It should be noted that this system may also compute a registration transform wherein this computation includes minimizing a set of Euclidean distances.

In some instances the computation of a registration transform may further comprise iteratively inputting registration transforms into a cost minimization function. In yet other instances the set of Euclidean distances may include at least the distances between the surface traces and the surface. In some embodiments the processor is programmed with further instructions comprising: initialize a fiducial position acquisition, record the position of the pointer tool during the fiducial position acquisition, and receive the location of fiducials points in the patient image. In alternate embodiments the set of Euclidean distances may include at least the distances between the surface traces and the surface and the distances between the fiducial positions and the fiducial points. In still yet alternate embodiments the processor is programmed with further instructions comprising: monitor the position of the pointer tool with the tracking system by recording the pointer tool positions, analyze the pointer tool positions to determine if the pointer tool is motionless, and upon determining that the pointer tool is motionless for a predetermined amount of time prompting the processor to initialize the surface trace acquisition.

Furthermore the processor is programmed with further instructions comprising: receiving input from a user ranking the one or more surface traces, computing a weighting for the surface traces based on the ranking, applying the weighting to the surface traces, and computing a registration transform that minimizes a set of Euclidean distances between the one or more surface traces and the surface. Again the processor may in some instances be programmed with further instructions comprising: receiving input from a user of one or more regions of one or more surface traces to be culled, discarding the one or more regions from the one or more surface traces, and computing a registration transform that minimizes a set of Euclidean distances between the one or more surface traces and the surface after the regions have been discarded.

The system as described herein my in some instances also comprise a display having a GUI for receiving input from a user, while the processor is programmed with further instructions to: initializing one or more landmark acquisitions, recording the positions of one or more landmarks on a patient, receiving the position of one or more landmark points in the patient image; and computing an initial registration transform that minimizes a set of Euclidean distances between the one or more landmarks and the one or more landmark points. In yet further embodiments the processor is programmed with further instructions comprising: using the initial registration transform to visualize, on the display, an initial alignment of the patient's position with the patient image in an image space and to visualize the surface traces on the display.

In an embodiment of the present disclosure, a surgical navigation system, usable for navigated surgical procedures, comprises: a tracked pointer tool for identifying positions on the patient; a tracking system for tracking the pointer tool; a processor programmed with instruction to: initialize a surface trace acquisition; continuously record the positions of the pointer tool during the surface; trace acquisition; combine the positions recorded during the surface trace acquisition into a surface trace; terminate the surface trace acquisition; receive a patient image of the patient; extract a surface from the patient image; compute a registration transform between the one or more surface traces and the surface for patient registration, the patient registration dynamically updated during the surface trace acquisition; segment the patient image into a plurality of regions, each region of the plurality of regions containing an anatomical landmark; determine a spatial distribution of surface traces among the plurality of regions; determine whether the spatial distribution in relation to each region of the plurality of regions minimizes deviance below a threshold; and if the spatial distribution in relation to any region of the plurality of regions is determined as exceeding the threshold, provide information relating to such region.

In an embodiment of the present disclosure, a method of performing a patient registration using a surgical navigation system, having a processor, in a medical procedure, comprises: initializing a surface trace acquisition; recording one or more surface traces; terminating the surface trace acquisition; receiving a patient image of a patient anatomy; extracting a surface from the patient image; computing a registration transform for patient registration between the one or more surface traces and the patient image extracted surface, the patient registration dynamically updated during the surface trace acquisition; segmenting the patient image into a plurality of regions, each region of the plurality of regions containing an anatomical landmark; determining a spatial distribution of surface traces among the plurality of regions; determining whether the spatial distribution in relation to each region of the plurality of regions minimizes deviance below a threshold; and if the spatial distribution in relation to any region of the plurality of regions is determined as exceeding the threshold, providing information relating to such region.

In an embodiment of the present disclosure, a method of fabricating a surgical navigation system, usable for navigated surgical procedures, comprises: providing a tracked pointer tool for identifying positions on the patient; a tracking system for tracking the pointer tool; and providing a processor programmed with instruction to: initialize a surface trace acquisition; continuously record the positions of the pointer tool during the surface; trace acquisition; combine the positions recorded during the surface trace acquisition into a surface trace; terminate the surface trace acquisition; receive a patient image of the patient; extract a surface from the patient image; compute a registration transform between the one or more surface traces and the surface for patient registration, the patient registration dynamically updated during the surface trace acquisition; segment the patient image into a plurality of regions, each region of the plurality of regions containing an anatomical landmark; determine a spatial distribution of surface traces among the plurality of regions; determine whether the spatial distribution in relation to each region of the plurality of regions minimizes deviance below a threshold; and if the spatial distribution in relation to any region of the plurality of regions is determined as exceeding the threshold, provide information relating to such region.

In an embodiment of the present disclosure, a method of dynamically updating a registration real time during a surface trace acquisition, via at least one of a user interface and a user interaction, comprises: selecting a registration technique from one of a touchpoint fiducial registration and a surface-trace technique; if the touchpoint fiducial registration technique is selected, selecting a fiducial marker; registering the fiducial marker; running an executable instruction comprising a fiducial-matching algorithm; updating a current registration; and observing and determining whether the current registration is sufficiently accurate within a predetermined accuracy range; if the current registration is sufficiently accurate, reviewing and determining whether the current registration is sufficiently accurate within a predetermined accuracy range; if the current registration is insufficiently accurate and another fiducial marker is available, selecting a fiducial marker; and if the current registration is insufficiently accurate and another fiducial marker is unavailable, commencing tracing a surface; and if the surface-trace technique is selected, iteratively touching and registering a plurality of facial features until a sufficient number of facial features are captured; if the sufficient facial features are captured, reviewing and determining whether the initial registration is adequate; if the initial registration is adequate, accepting the initial registration; and commencing tracing a surface; and, if the initial registration is inadequate, iteratively touching and registering a plurality of facial features until a sufficient number of facial features are captured.

Some of the features in the present disclosure are broadly outlined in order that the section entitled Detailed Description is better understood and that the present contribution to the art is better appreciated. Additional features of the present disclosure are described hereinafter. In this respect, understood is that the present disclosure is not limited in its application to the details of the components or steps set forth herein or as illustrated in the several figures of the being carried out in various ways. Also, understood is that the phraseology and terminology employed herein are for the purpose of the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

Figure 1:
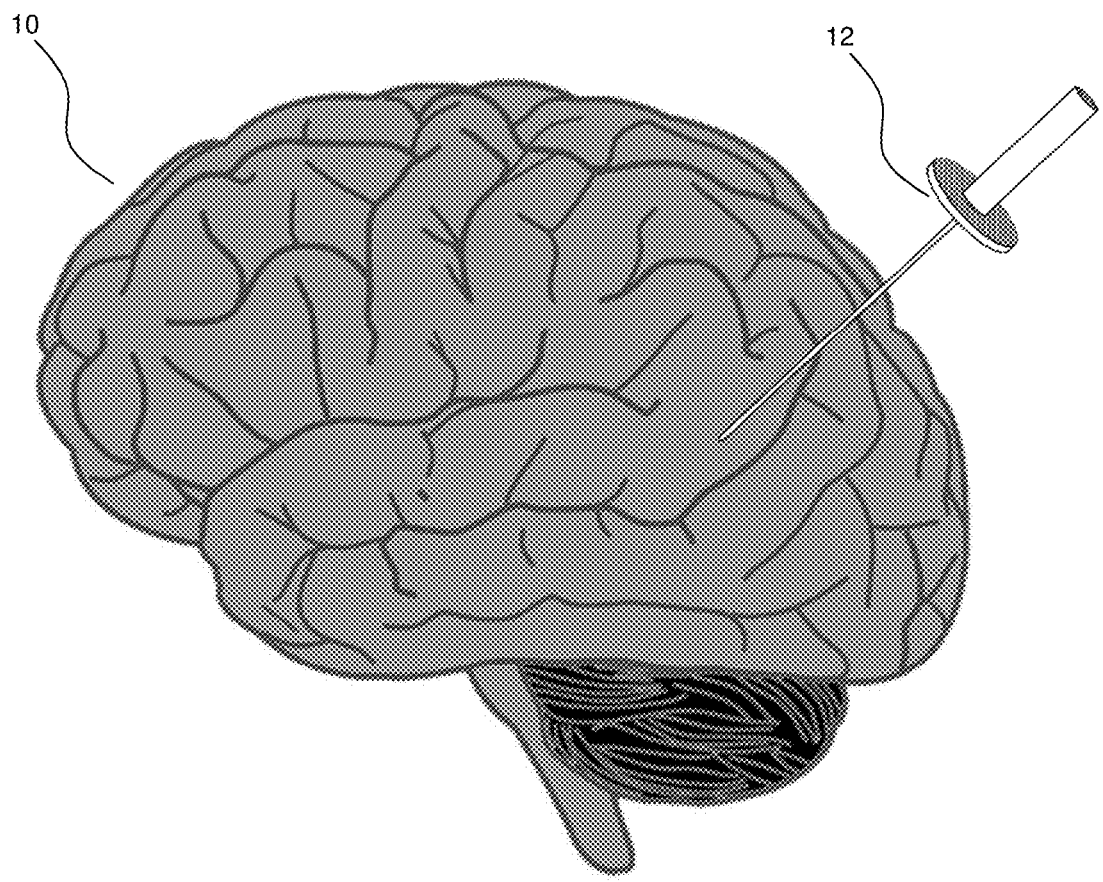
FIG. 1 is a diagram illustrating insertion of an access port into a human brain for providing access to internal brain tissue during a medical procedure, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures is emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" denotes "serving as an example, instance, or illustration," and should not be construed as preferred or advantageous over other configurations disclosed herein.

As used herein, the terms "about," "approximately," and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e g minimally invasive medical procedures) are performed based on access to internal tissue through the access port.

The present disclosure is generally related to medical procedures, neurosurgery, and patient registration to be specific. In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

Referring to FIG. 1, this diagram illustrates insertion of an access port into a human brain for providing access to internal brain tissue during a medical procedure, in accordance with an embodiment of the present disclosure. The access port 12 is inserted into a human brain 10, providing access to internal brain tissue. Access port 12 may include instruments such as catheters, surgical probes, or cylindrical ports such as the NICO BrainPath®. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed. In the example of a port-based surgery, a straight or linear access port 12 is typically guided down a sulci path of the brain. Surgical instruments would then be inserted down the access port 12.

Still referring to FIG. 1, optical tracking systems, usable in the medical procedure, track the position of a part of the instrument that is within line-of-site of the optical tracking camera. In some embodiments these optical tracking systems also require a reference to the patient to know where the instrument is relative to the target, e.g., a tumor, of the medical procedure. These optical tracking systems require a knowledge of the dimensions of the instrument being tracked so that, for example, the optical tracking system knows the position in space of a tip of a medical instrument relative to the tracking markers being tracked.

Figure 2:
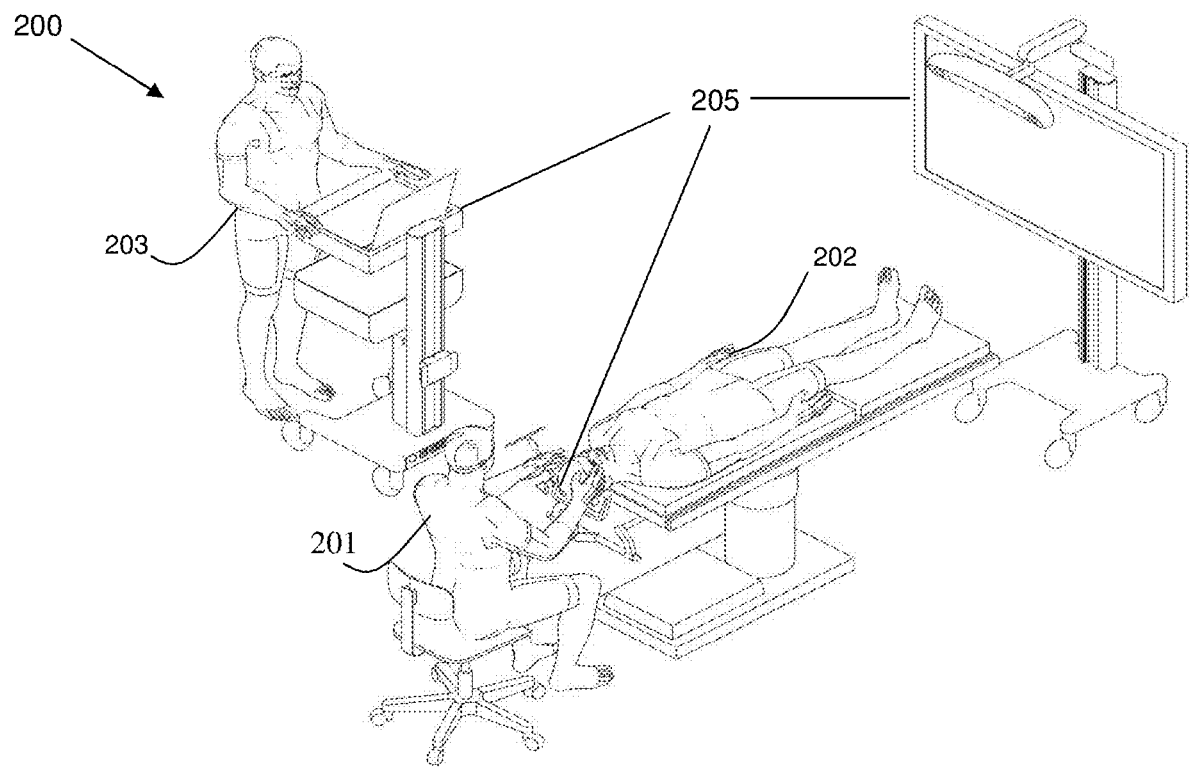
FIG. 2 is a diagram illustrating an exemplary navigation system to support minimally invasive access port-based surgery, in accordance with an embodiment of the present disclosure.

Referring to FIG. 2, this diagram illustrates an exemplary navigation system to support minimally invasive access port-based surgery, in accordance with an embodiment of the present disclosure. An exemplary navigation system environment 200 is usable to support navigated image-guided surgery. A surgeon 201 conducts a surgery on a patient 202 in an operating room (OR) environment. A medical navigation system 205 comprising an equipment tower, tracking system, displays, and tracked instruments assists the surgeon 201 during this procedure. An operator 203 is also present to operate, control, and provide assistance for the medical navigation system 205.

Figure 3:
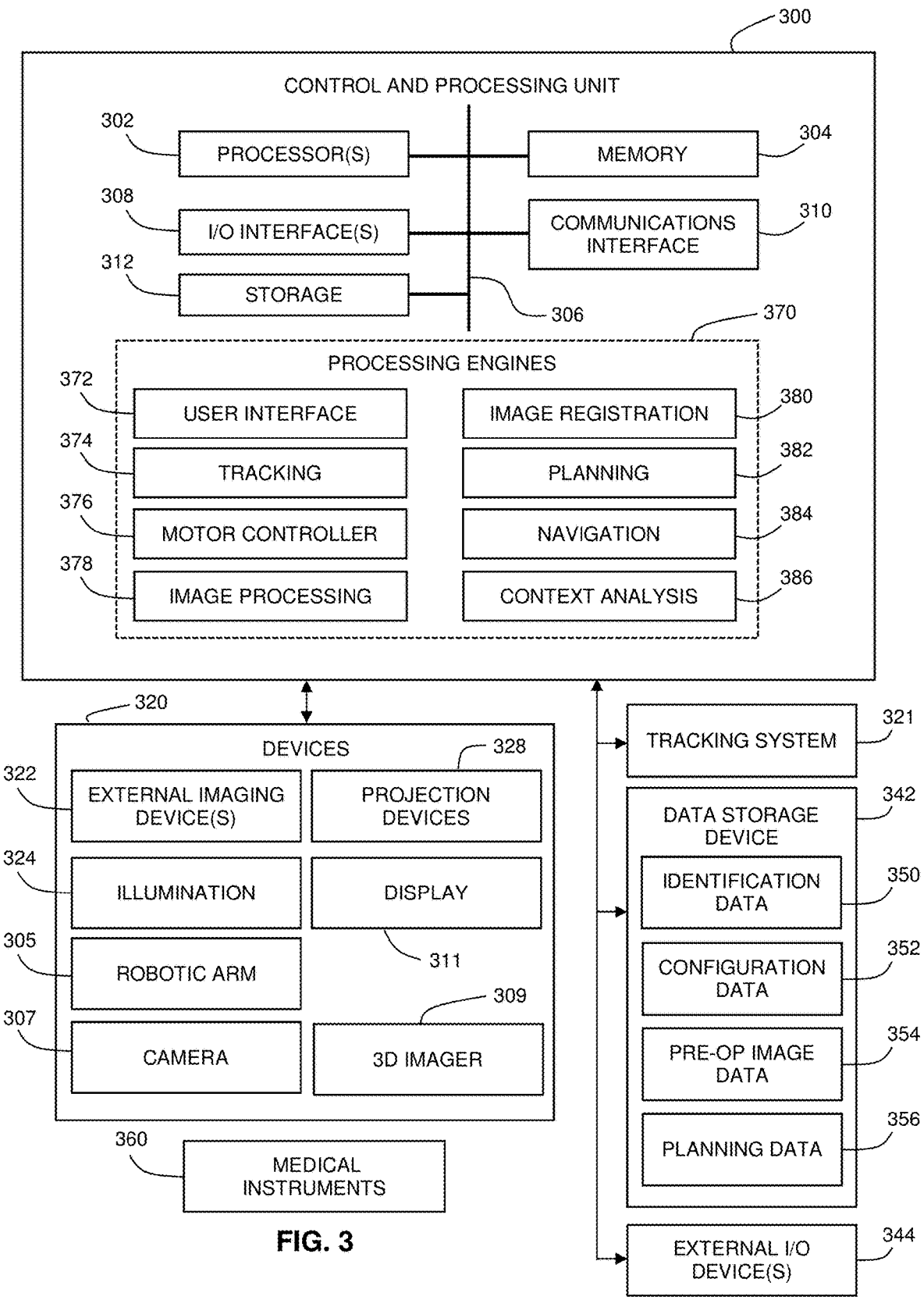
FIG. 3 is a block diagram illustrating a control and processing system that is used in the navigation system, as shown in FIG. 2, in accordance with an embodiment of the present disclosure.

Referring to FIG. 3, this block diagram illustrates a control and processing system that is used in the navigation system, as shown in FIG. 2, in accordance with an embodiment of the present disclosure. A control and processing system 300 is usable in the medical navigation system 200, e.g., as part of the equipment tower. In one example, control and processing system 300 may include one or more processors 302, a memory 304, a system bus 306, one or more input/output interfaces 308, a communications interface 310, and storage device 312. Control and processing system 300 is interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 is any suitable data storage device, such as a local or remote computing device, e.g. a computer, hard drive, digital media device, or server, having a database stored thereon. Data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 is provided as multiple storage devices.

Still referring to FIG. 3, medical instruments 360 are identifiable by control and processing unit 300. Medical instruments 360 is connected to and controlled by control and processing unit 300, or medical instruments 360 is operated or otherwise employed independent of control and processing unit 300. Tracking system 321 is employed to track one or more of medical instruments 360 and spatially register the one or more tracked medical instruments to an intraoperative reference frame. For example, medical instruments 360 may include tracking markers such as tracking spheres that is recognizable by a tracking camera 307. In one example, the tracking camera 307 is an infrared (IR) tracking camera. In another example, as sheath placed over a medical instrument 360 is connected to and controlled by control and processing unit 300.

Still referring to FIG. 3, control and processing unit 300 interfaces with a number of configurable devices and intraoperatively reconfigures one or more of such devices, based on configuration parameters obtained from configuration data 352. Examples of devices 320 include one or more external imaging devices 322, one or more illumination devices 324, a robotic arm 305, one or more projection devices 328, a 3D imager 309, and one or more displays 311. Noted is that the 3D imager includes devices, such as a preoperative or intraopertive CT, MRI, Ultrasound, OCT, or Structured light imaging probes, and the like.

Still referring to FIG. 3, exemplary aspects of the disclosure are implementable via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 is stored in the memory 304 and the processing modules is collectively referred to as processing modules 370.

Still referring to FIG. 3, understood is that the system is not intended to be limited to the components shown in FIG. 3. One or more components of the control and processing system 300 is provided as an external component or device. In one example, navigation module 384 is provided as an external navigation system that is integrated with control and processing system 300.

Still referring to FIG. 3, some embodiments is implemented using processor 302 without additional instructions stored in memory 304. Some embodiments is implemented using the instructions stored in memory 304 for execution by one or more general purpose microprocessors. Thus, the disclosure is not limited to a specific configuration of hardware and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution.

Still referring to FIG. 3, according to one aspect of the present disclosure, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure is applied to any suitable medical procedure. While one example of a navigation system 205 is provided that is used with aspects of the present application, any suitable navigation system is used, such as a navigation system using optical tracking instead of infrared cameras.

Figure 4A:
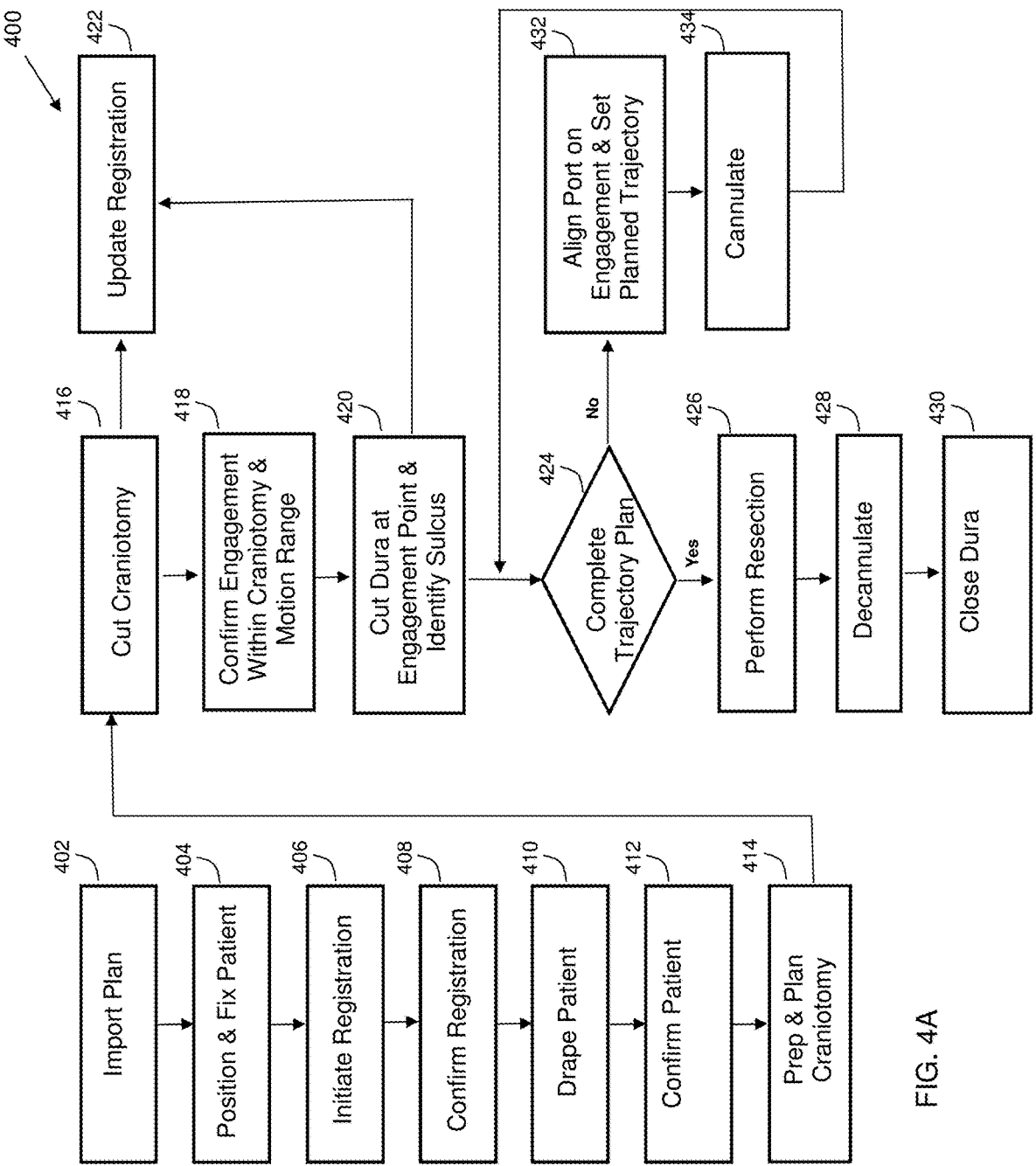
FIG. 4A is a flow diagram illustrating a method of performing a port-based surgical procedure using a navigation system, as shown in FIG. 2, in accordance with an embodiment of the present disclosure.

Referring to FIG. 4A, this flow diagram illustrates a method 400 of performing a port-based surgical procedure using a navigation system 205, as shown in FIG. 2, in accordance with an embodiment of the present disclosure. At a first block 402, the port-based surgical plan is imported. A detailed description of the process to create and select a surgical plan is outlined in International Publication No. WO/2014/139024, entitled "PLANNING, NAVIGATION AND SIMULATION SYSTEMS AND METHODS FOR MINIMALLY INVASIVE THERAPY," claiming priority to U.S. Provisional Patent Application Ser. Nos. 61/800,155 and 61/924,993, all of which are herein, and hereby, incorporated by reference in their entirety. Once the plan has been imported into the navigation system at the block 402, the patient is placed on a surgical bed. The head position is confirmed with the patient plan in the navigation system (block 404), which in one example is implemented by a computer or controller forming part of the equipment tower.

Still referring to FIG. 4A, next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is usable for medical imaging in which images from different imaging modalities are co-registered. In some instances registration may also be used in order to be able to compare, map, or integrate the data obtained from these different modalities with a position of a patient in physical space.

Still referring to FIG. 4A, numerous registration techniques available and one or more of these techniques is implementable to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images is co-registered, while multi-modality registration methods are used to register images acquired by different scanner or sensor types, for example in magnetic resonance imaging (MRI) and positron emission tomography (PET). In the present disclosure, multi-modality registration methods is used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT to patient in physical space.

Figure 4B:
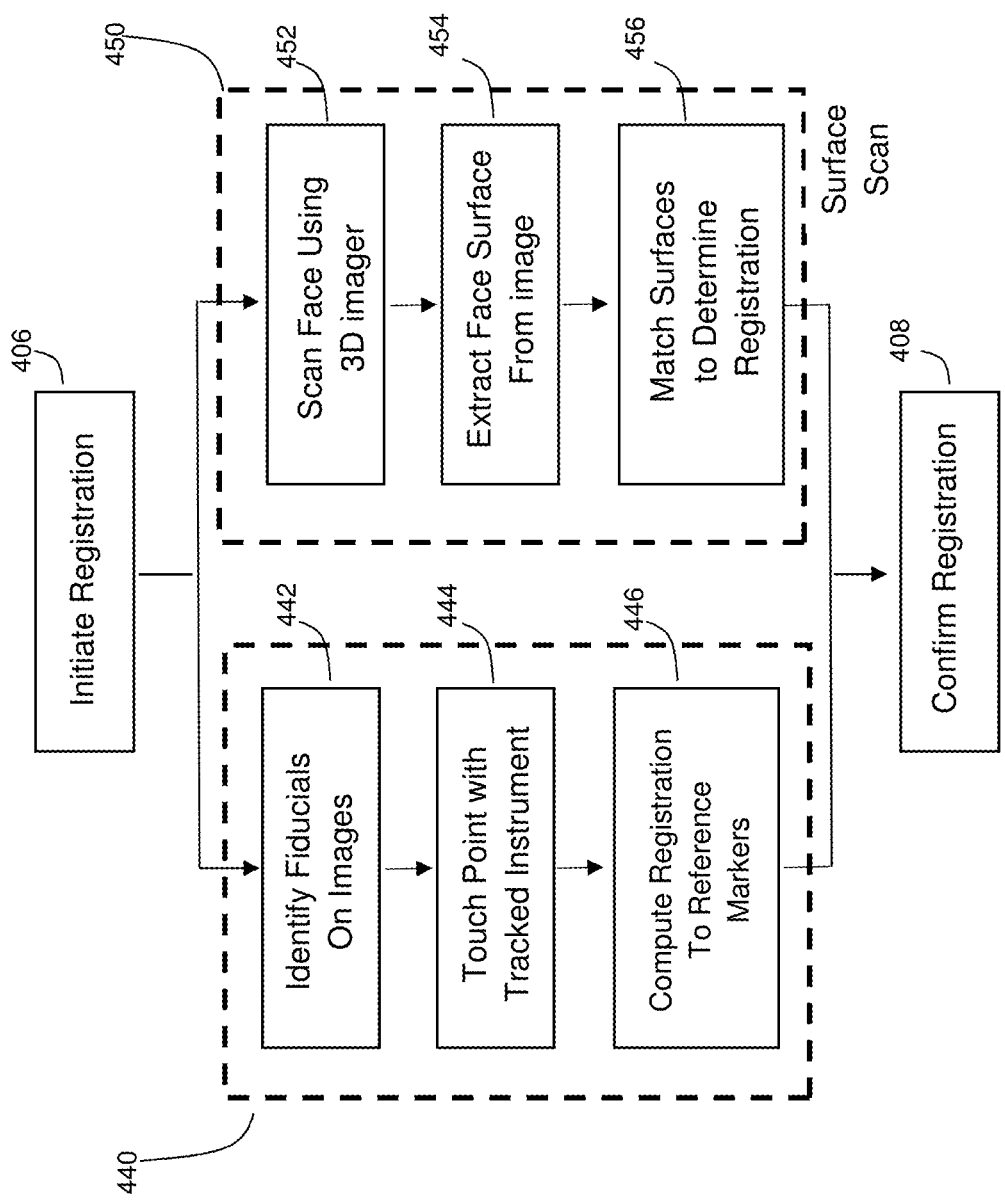
FIG. 4B is a flow diagram illustrating a method of registering a patient for a surgical procedure, as shown in FIG. 4A, in accordance with an embodiment of the present disclosure.

Referring to FIG. 4B, this flow diagram illustrates, in greater detail, two methods, e.g., a fiducial touch points procedure 440 and a surface scan procedure 450, of registering a patient for a surgical procedure, as shown in FIG. 4A, that are performable as per registration block 406, in accordance with an embodiment of the present disclosure. If the use of fiducial touch points (440) is contemplated, the method involves first identifying fiducials on images (block 442), then touching the touch points with a tracked instrument (block 444). Next, the navigation system computes the patient registration to reference markers (block 446). Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods are usable to minimize the displacement of the new sterile patient reference relative to the non-sterile one that has been used for registration. However, inevitable is that some error will exist. This error directly translates into registration error between the surgical field and pre-surgical images. In fact, generally the further away points of interest are from the patient reference, the worse the error will be.

Still referring back to FIG. 4A, upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain (block 416). Registration data is updated with the navigation system at this point (block 422). Next, the engagement within craniotomy and the motion range are confirmed (block 418). Next, the procedure advances to cutting the dura at the engagement points and identifying the sulcus (block 420).

Still referring back to FIG. 4A, thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424). Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks is skipped or suitably modified when performing non-port based surgery.

Figure 5:
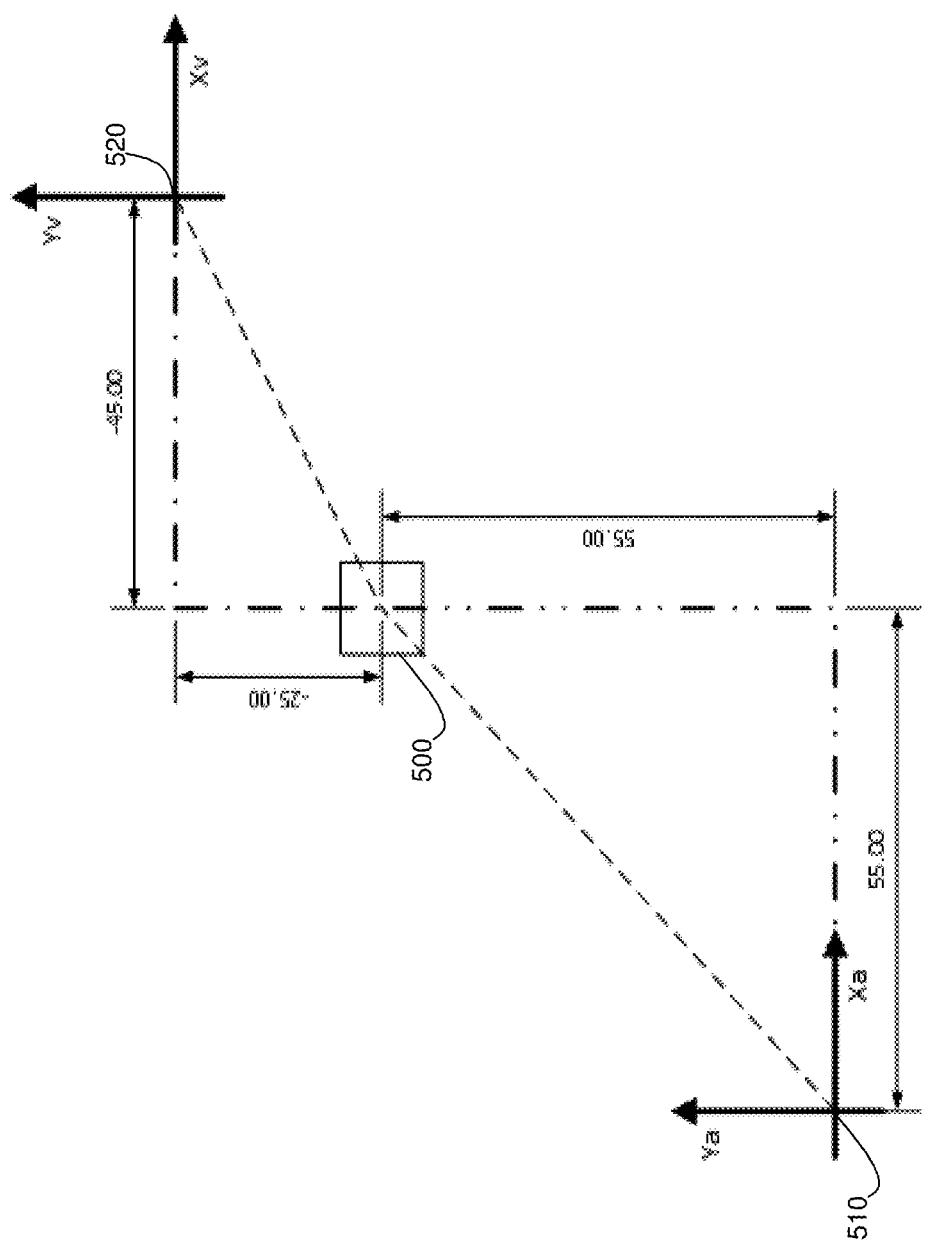
FIG. 5 is an explanatory diagram illustrating details regarding the coupling of two coordinate spaces, in accordance with an embodiment of the present disclosure.

Referring to FIG. 5, this explanatory diagram illustrates details regarding the coupling of two coordinate spaces, in accordance with an embodiment of the present disclosure. A registration process, similar to that which is used in block 456 of FIG. 4B, is shown for computing a transform that is used to import coordinates from the physical coordinate space of the operating room to the image space of the MRI image. Resultantly any tool positions in the physical coordinate space is registered to the image space via the application of this transform.

Still referring to FIG. 5, in order to derive this transform for importing objects from a physical coordinate space to an image space, the two spaces must be coupled with a "common reference", having a defined position that can be located in both the physical and image coordinate spaces. The process of patient registration for surgical navigation uses identifiable points located on a patient anatomy visible both on the patient and on the patients scan as the common reference point(s). An example of a common reference 500 is shown along with the physical and image coordinate space origins, 510 and 520 respectively. The common references position is known in both spaces. Using these positions, a transform is derived that facilitates the importation of the position of any point in the physical coordinate space into the image space. One way to determine the transform is by equating the locations of the common reference in both spaces and solving for an unknown translation variable for each degree of freedom defined in the two coordinate spaces. These translation variables may then be used to convert a set of coordinates from one space to the other.

Still referring to FIG. 5, an exemplary transform is derived. In the figure the position of the common reference 500 is known relative to the physical coordinate space origin 510 and the image space origin 520. The common references position can be extracted from the diagram as follows: $(X_{cra}, Y_{cra})=(55, 55)$ and $(X_{crv}, Y_{crv})=(-45, -25)$, wherein the subscript "cra" denotes the common reference position relative to the physical coordinate space origin and the subscript "crv" denotes the common reference position relative to the image space origin. Utilizing a generic translation equation describing any points $((Y_a, X_a)$ and $(Y_v, X_v))$, where the subscript "a" denotes the coordinates of a point relative to the physical coordinate space origin 510, and the subscript "v" denotes the coordinates of a point relative to the image space origin 520, we can equate the individual coordinate elements from each space to solve for translation variables $((Y_T, X_T))$, wherein the subscript "T" denotes the translation variable as follows:

$$Y_v = Y_a + Y_T$$

$$X_v = X_a + X_T$$

Still referring to FIG. 5, now substituting the derived values of the points, we can solve for the translation variable is solvable as follows:

$$-45 = 55 + Y_T$$

$$100\ Y_T$$

and $$-25 = 55 + X_T$$

$$80 = X_T.$$

Still referring to FIG. 5, utilizing these translation variables, any position, e.g., $(Y_a, X_a)$ defined relative to the common reference in the physical coordinate space is transformed into an equivalent position defined relative to the common reference in the image space through the two generic transformation equations provided below. Noted is that these following equations are rearranged to transform any coordinates of a position from the image space into equivalent coordinates of a position in the physical coordinate space as well:

$$X_a = X_v + 100$$

and $$Y_a = Y_v + 80.$$

Still referring to FIG. 5, the calculated transform thus enables the position of any object to be transformed from the physical coordinate space to the image space. Thus, the two spaces become coupled with the transform enabling the registration of objects from the physical space to the image space. Noted is that in practice the common reference is usually a set of points (as opposed to a single point) from the patients anatomy that is located both on the anatomy of the patient in the physical coordinate space of the operating room and in the image of the patient. Using a set of points is more advantages as it further restricts degrees of freedom. More specifically in a spatial coordinate system such as the physical coordinate space of the operating room an object may have six degrees of freedom, three spatial degrees of freedom most commonly referred to as (x, y, z) and three rotational degrees most commonly referred to as (pitch, yaw, roll). Accordingly, one manner to duplicate these values upon transformation from the physical coordinate space to the image space is to transform three or more points from the object.

Figure 6:
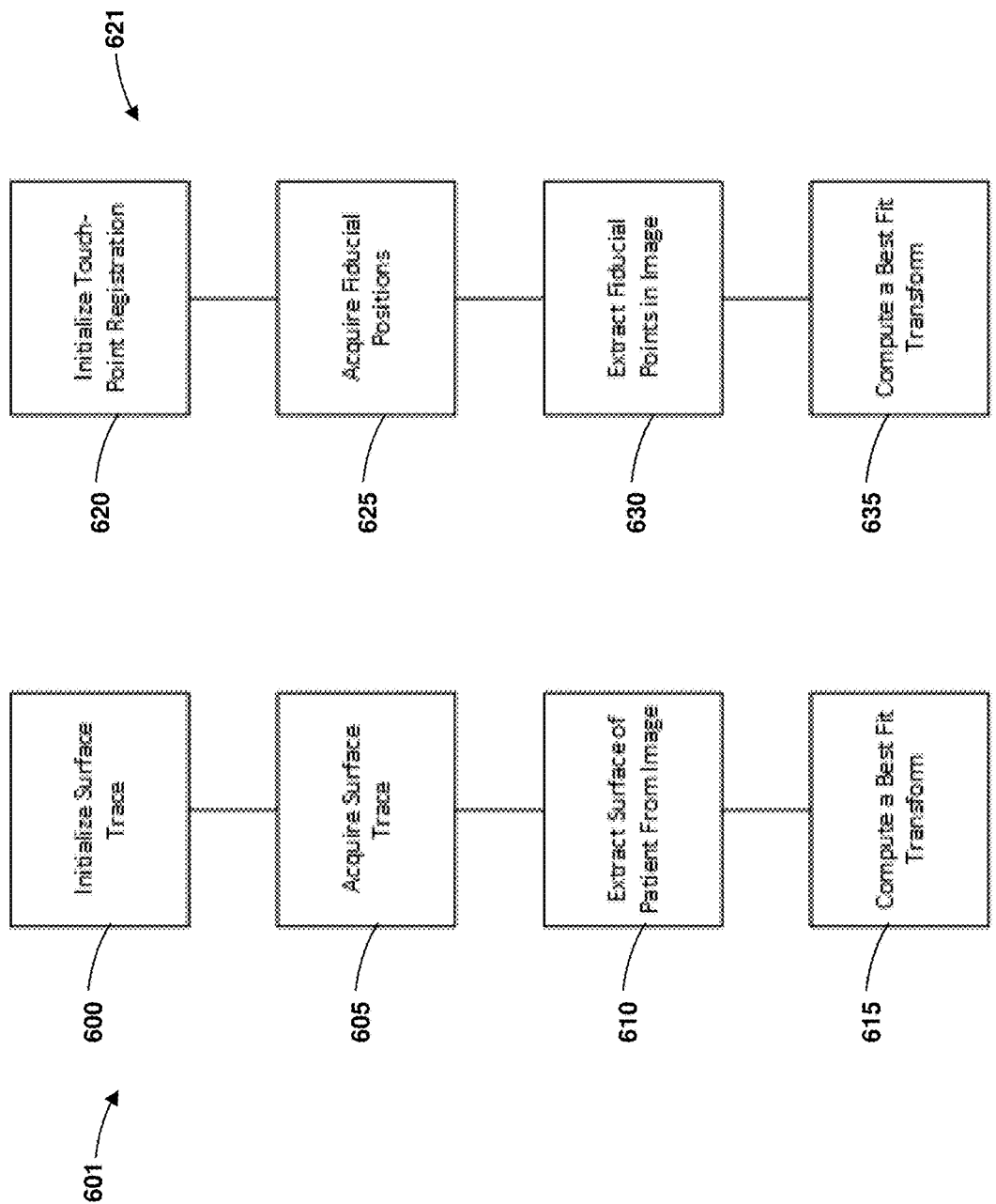
FIG. 6 is a flow diagram illustrating two methods of registering a patient for a medical procedure with a medical navigation system, in accordance with an embodiment of the present disclosure.
Figure 7:
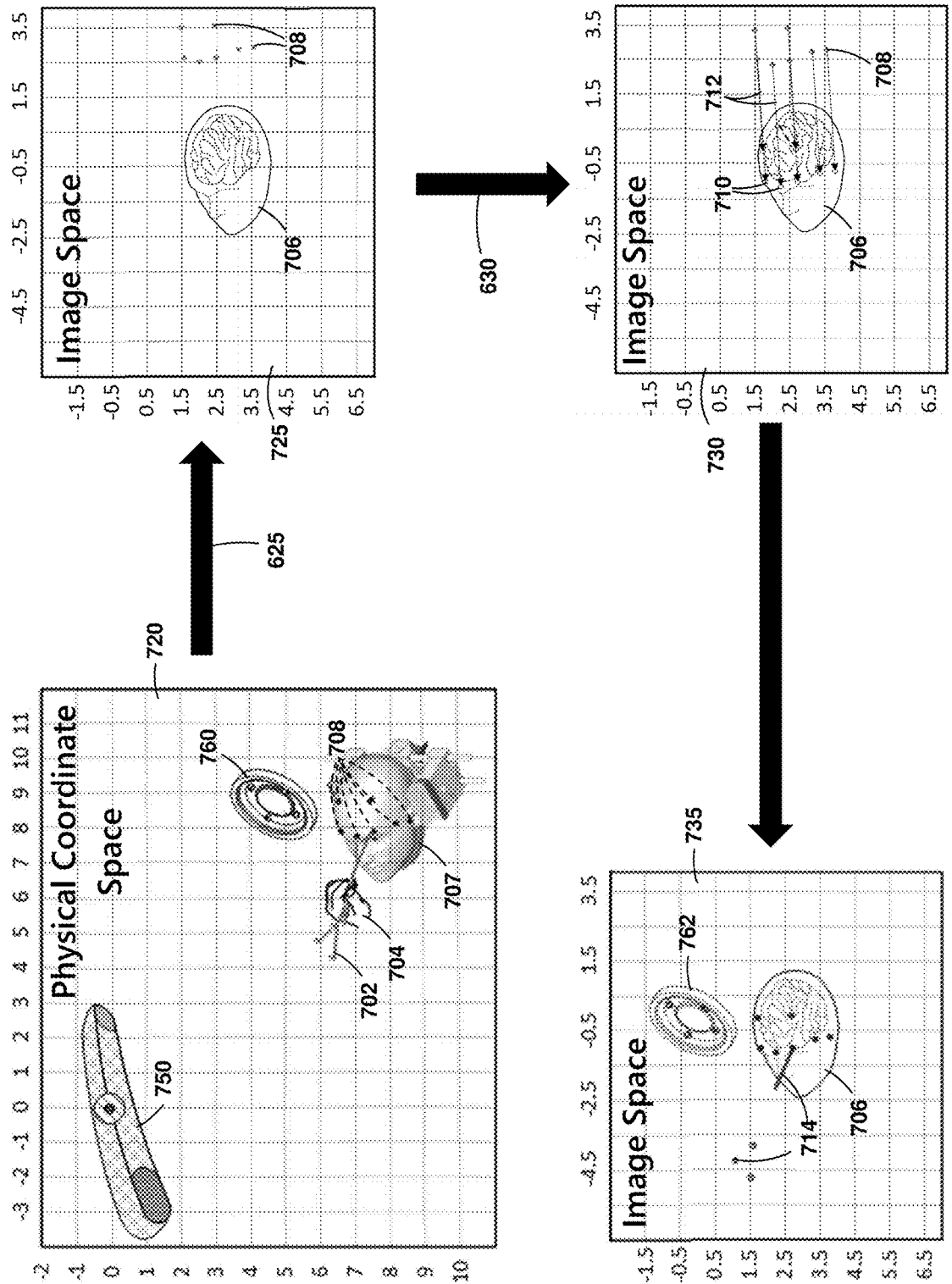
FIG. 7 is a diagram illustrating one of the methods, as shown in FIG. 6, in accordance with an embodiment of the present disclosure.

Referring to FIGS. 6 and 7, together, this flow diagram illustrates two methods of registering a patient for a medical procedure with a medical navigation system, in accordance with embodiments of the present disclosure. To further elaborate on the process of registration two practical implementations will be described in further detail as follows. Referring to FIG. 6, the first method 621 is the touch-point registration method and the second method 601 is the more recently established surface trace method. Referring to FIG. 7, this diagram illustrates one of the methods, as shown in FIG. 6, in accordance with an embodiment of the present disclosure. Each step in performing a registration is shown using the touch-point method 621. These methods is employed through the use of the navigation system and any steps is programmed into the processor and stored in memory and called upon when needed.

Still referring to FIGS. 6 and 7, together, the first step in this method 620 is to initiate the touch-point acquisition process. During this step, a user may prompt the navigation system processor, such as processor 302 in FIG. 3, to initiate a touch-point acquisition process. To clarify a touchpoint acquisition may refer to the priming of the system to acquire a pointer position upon determining it to be at the position of a fiducial point. In an alternate embodiment the system itself may initiate a touch-point registration process without the input of the user, such as upon the system advancing to the touch-point registration mode, or upon detection of trackable medical instruments such as by tracking system 321.

Referring to FIG. 7, once the touch-point registration process is initiated 620 the following step is to acquire one or more fiducial positions 625 in the physical coordinate space of the operating room. FIG. 7 depicts an illustration of this step 625. As is shown in the figure a user 704 is identifying fiducials 708 on a patient 707 using a tracked pointer tool 702. The tracking camera 750, connected to the surgical navigation system (not shown), collects the positions of the fiducial points 708 via the tracked pointer tool 702 and passes them to the navigation system processor which either stores the points in the image space containing the patient image, such as the points 708 in the image space 725, or alternatively in memory, or the like. In some cases the tracking system is constantly tracking the pointer tool's position. Thus in order to record the position of the pointer tool at the correct time e.g., when it is placed on a fiducial), the system is prompted by the user. This prompt is facilitated through the use of a switch type device such as a foot pedal or mouse that is connected to the surgical navigation system and are read by the processor for activation. In addition an alternate way of prompting the navigation system to record the position of the pointer tool when placed on the fiducial is through the use of a gesture. One gesture that is used to capture the position of the pointer tool at the correct time is statically holding the pointer tool in the same position for a predetermined amount of time. One benefit of using this gesture based switch over the manual ones is that it requires no additional hardware and is implemented using the navigation system with the hardware as is.

Still referring to FIG. 7, once the fiducial points are acquired 625 the following step is to extract the scanned fiducial points from the patient image 630. FIG. 7 depicts an illustration of this step. As is shown in the figure the scanned fiducials 710 are segregated from the rest of the patient image 706 in the image space 730. In some cases the segregation of the fiducials from the image of the patient is completed manually by a user, where the user indicates the fiducial positions on the patient image to the surgical navigation system through a graphical user interface, such as 372 in FIG. 3. While in other cases the surgical navigation system is programmed with instructions to segregate the positions of the scanned fiducials from the patient image automatically. Thus step 630 is performed by either a user or a surgical navigation system.

Still referring to FIG. 7, once the scanned fiducial points are extracted from the patient image 630, the following step 635 is to compute a patient registration transform. FIG. 7 depicts an illustration of a computed transform 712 as per the example provided. It is apparent from the figure that the transform 712 is computed such that the fiducial points 708 acquired from the physical coordinate space align with the extracted fiducials 710. In general the completion of this step 635 requires the navigation system processor to compute a single transform that when applied to each fiducial point 708 in the image space individually, will align them with their scanned fiducial counterparts 710. However given practical limitations of technology perfect alignment is problematic to achieve for all of the fiducial points using a single transform. Thus, to approximate a perfect alignment the processor instead computes a transform that minimizes the deviation in alignment between the extracted fiducials from the patient image and the fiducial points on the patient.

Figure 8:
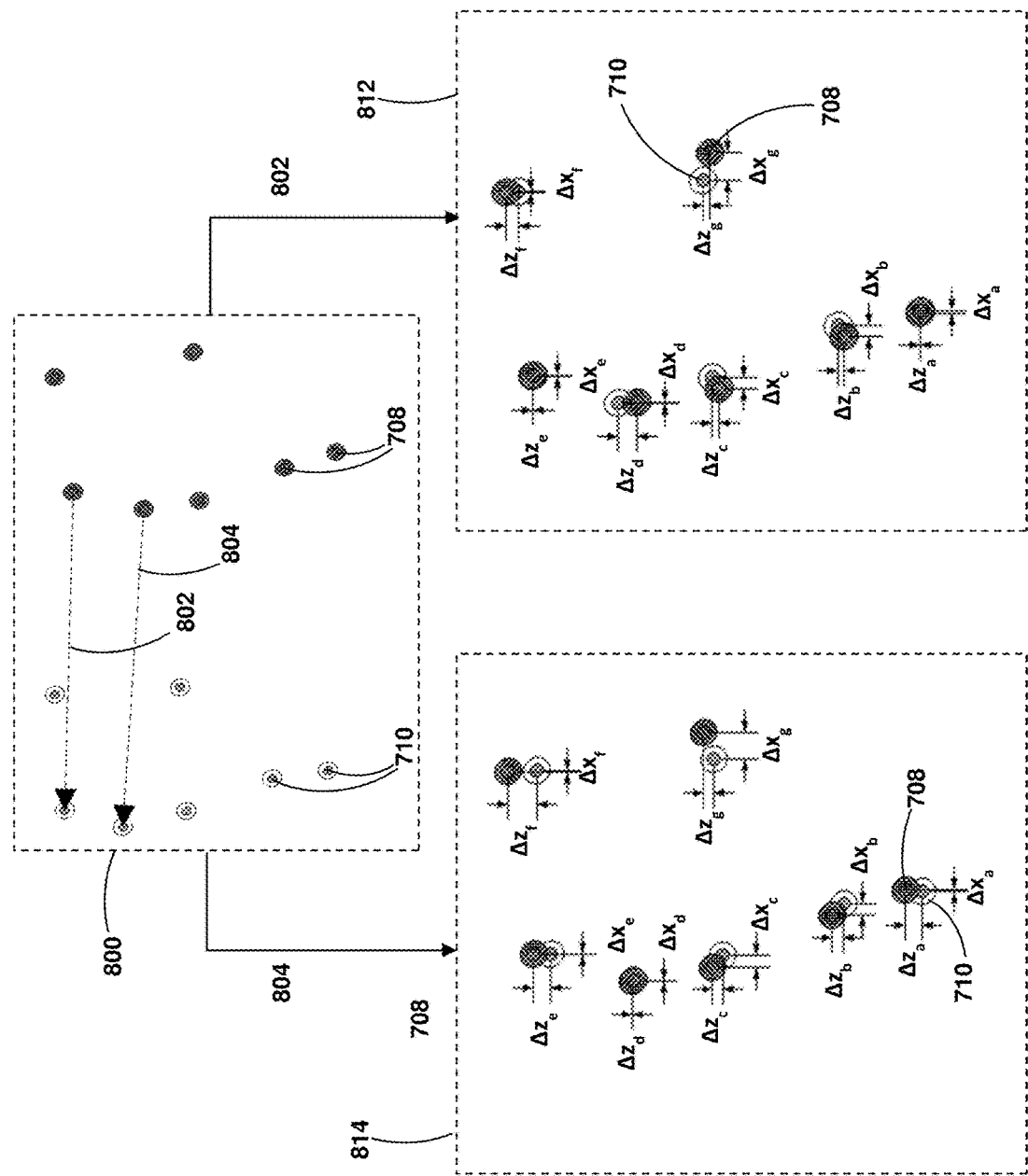
FIG. 8 is a diagram illustrating a transform by the method 621, as shown in FIG. 6, in accordance with an embodiment of the present disclosure.

Referring to FIG. 8, this diagram illustrates a transform by the method 621, as shown in FIG. 6, in accordance with an embodiment of the present disclosure. For example as shown in FIG. 8 the transforms 802 and 804 both attempt to align the fiducial points 708 with their counterparts 710 in the image space 800. Such transforms is derived by iteratively applying a cost minimization function to the initial set of fiducial points with arguments being the sum of spatial deviances $\Delta x_{a \to g}$ and $\Delta z_{a \to g}$ between the two sets of points 708 and 710. For example, as shown in FIG. 8, the iterative computation may in one iteration produce the transform 804 that when applied to the fiducial points 708 produces the alignment of points shown in frame 814 of FIG. 8. While in a subsequent iteration may produce the transform 802 that when applied to the fiducial points 708 produces the alignment of points shown in frame 812 of FIG. 8. The processor may then execute the cost minimization function to compare the sum of the deviances $\Delta x_{a \to g}$ and $\Delta z_{a \to g}$ for each result 814 and 812 and select the one with the lowest value for the next iteration and so on until the deviation value falls below a certain threshold value or meets some alternately defined criteria. It is apparent from the case shown in FIG. 8 that the transform which minimizes the spatial deviances $\Delta x_{a \to g}$ and $\Delta z_{a \to g}$ when applied to the fiducial points 708 is the transform 812. It should be noted that in the example provided in the figure the deviances are shown in two dimensions however this should not be taken to limit the number of dimensions over which these iterative cost minimization functions is applied.

Referring back to FIGS. 6 and 7, once step 635 is completed and a patient transform is derived (FIG. 6), it may then be used to transform any points from the physical coordinate space of the operating room into the image space, effectively coupling the two spaces. In FIG. 7, this aspect of the patient registration process is illustrated by the physical coordinate space 720 and the image space 735 where the spatial alignments between the patient 707, the patient reference 760, and the pointer tool 702 is duplicated by the virtual representations of these objects in the image space 735. i.e. by the patient scan 706, the virtual patient reference 762 and the virtual pointer tool 714 in the image space 735. Returning to the flow charts in FIG. 6, the second flow chart 601 describes the process of a surface trace patient registration.

Figure 9:
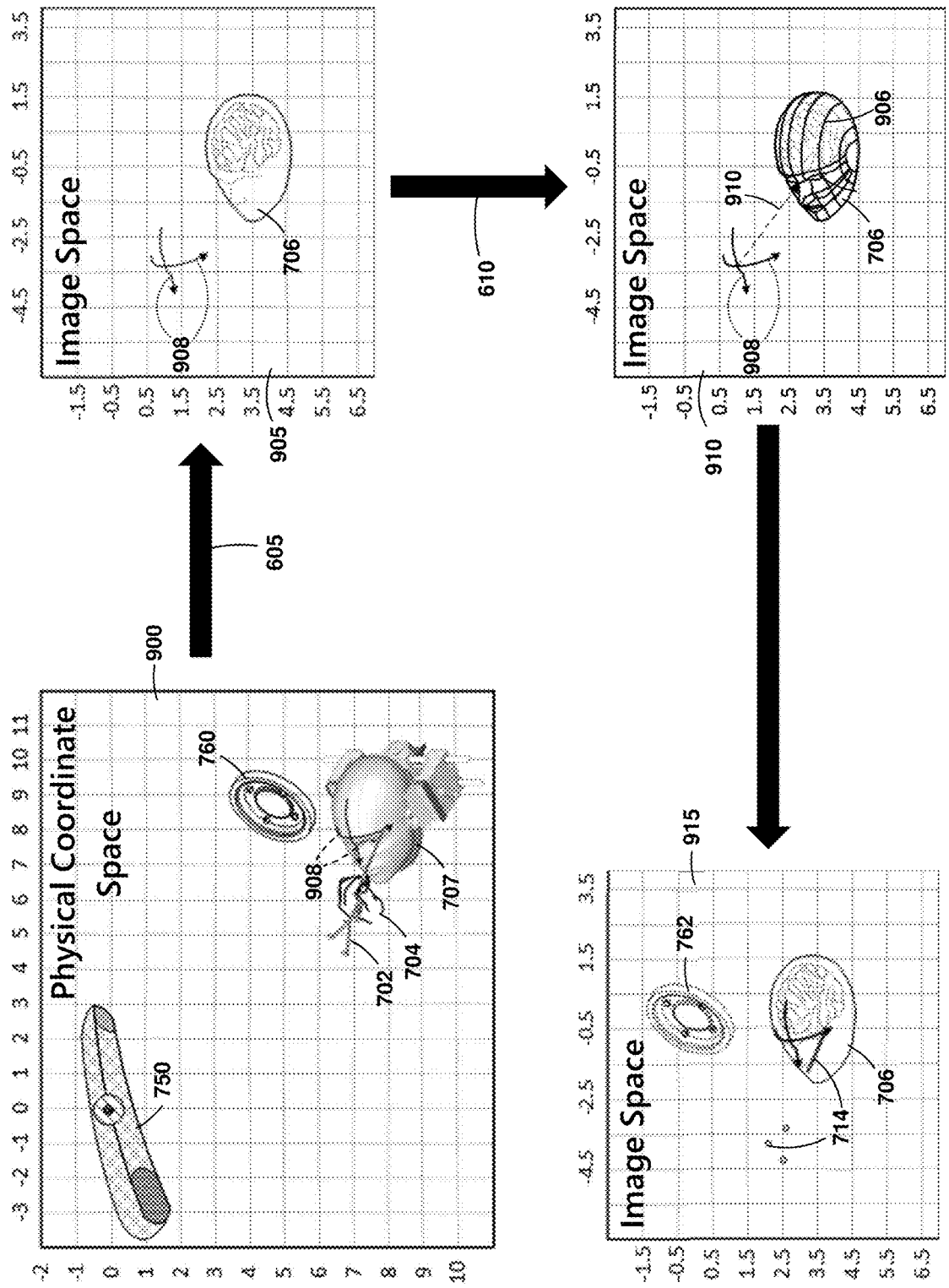
FIG. 9 is a diagram illustrating the method 601, as shown in FIG. 6, in accordance with an embodiment of the present disclosure.

Referring to FIG. 9, this diagram illustrates the method 601, as shown in FIG. 6, in accordance with an embodiment of the present disclosure. Each step in performing a patient registration using the surface trace method 601 is detailed. This method is implemented using a surgical navigation system, any steps that are programmed into the processor, and/or any instructions that are stored in memory and recalled therefrom as needed. The first step in this method 600 is to initialize the surface trace patient registration process. During this step a user may prompt the navigation system processor, such as processor 302 in FIG. 3, to prime itself to receive one or more surface traces of the patient. To clarify a surface trace generally refers to a set of point positions acquired sequentially, that are identified by guiding a tracked tool over the contours of a patient's surface features by the tracking system.

Still referring to FIG. 9, alternatively, to point positions any data type able to represent the contours of the patient is used instead, such as vectors, curves, and the like. In some instances, as opposed to the user initializing the surface trace patient registration process, an alternate embodiment would be the system itself may initiate a surface trace registration process without the input of the user, such as upon the system advancing to the patient registration step, or upon detection of trackable medical instruments in the operating room (for example, via tracking system 321), or upon other indicative actions. One such action could be detected by the navigation system, such as for example the navigation system determining that the pointer tool tip has dwelled at the same position for a predetermined period of time. To elaborate further, a user may allow the pointer to dwell in a position until the navigation system processor recognizes this action and begins serially acquiring positions of the pointer at which time the surgical navigation system may notify the user that it has begun capturing positions for the surface trace by producing an audible signal, or in an alternate embodiment may notify the user through the display and GUI of the navigation system.

Still referring to FIG. 9, in some instances, the surgical navigation system may indicate to the user that a trace has begun or ended using an audible signal such as a click or a continuous tone until the trace ends. The termination of a trace, e.g., the point at which the navigation system stops serially acquiring positions of the pointer tool, may in some instances be prompted by many of the trace inducers described above. Furthermore, in addition to dwelling, another gesture that is used to terminate the trace would be a fast movement of the pointer. This embodiment could be implemented by comparing each new position of the pointer in the series with the previous position of the pointer and checking to see if that value falls within some tolerance value. In yet another embodiment the trace may terminate if the pointer tool position becomes undetectable. For, example if the pointer tool leaves the field of view of the camera.

Still referring to FIG. 9, once the surface trace registration process is initiated 600 the following step 605 is to acquire one or more surface traces in the physical coordinate space of the operating room. A user 704 is guiding a tracked pointer tool 702 along the contours of a patient's face 707 to acquire the two surface traces 908. The tracking camera 750, connected to the surgical navigation system, collects the positions of the surface trace points 908 via the tracked pointer tool 702 and passes them to the navigation system processor which stores the points in the image space containing the patient image, such as the points 908 in the image space 905, in the processor memory, or alternatively any known coordinate space. In some instances the tracking system is continuously tracks the pointer tool's position in order to record the positions of the pointer tool during the surface trace, e.g., when it is guided across the features of the patient). During this instance the system is prompted by the user to begin or end the trace. This prompt is facilitated through the use of a switch type device, such as a foot pedal or mouse, coupled with the surgical navigation system or, in alternate embodiments, is determined by the inertial state of the pointer tool as determined by the tracking system component of the surgical navigation system. Noted is that further techniques for beginning or ending the trace are described herein and encompassed by the present disclosure.

Still referring to FIG. 9, once the surface traces are acquired 605 the following step 610 is to extract the surface from the patient image. The image of the surface 906 of the patient is extracted from the patient image 706 in the image space 910. In some cases the extraction of the surface from the image of the patient is completed by the combination of a user and a processor through a GUI. While in other cases the surgical navigation system is programmed with instructions to extract the surface of the patient from the patient image from automatically. In yet alternate cases the surface is provided in a useable form, e.g., to compute a surface trace patient registration via surface matching) by the 3D imager which acquired the image. Thus, the step 610 is performed by either a user or an automated system, such as a surgical navigation system processor.

Still referring to FIG. 9, once the surface of the patient is extracted from the patient image 610 the following step is to compute a patient registration transform 635. A computed transform 910, as per the example, is provided. The transform 910 is computed such that the surface traces 908, acquired from the physical coordinate space, align with the extracted surface contours 906 (and also consequently the patient image). In general, the completion of this step 635 requires the navigation system processor to compute a single transform that when applied to each surface trace 908 in the image space individually, will align them with the extracted surface 906 of the patient image 706. However given practical limitations of technology perfect alignment is problematic to achieve for all of the points (or equivalents) in one or more surface traces using a single transform. Thus, to approximate a perfect alignment, the processor, instead, derives a transform that minimizes the deviation in alignment between the surface 906 extracted from the patient image 706 and the surface traces 908 acquired from the patient.

Still referring to FIG. 9, however, given the practical limitations of perfect alignments other algorithmic variants is used alternatively to the minimization described above. For example, weighting certain traces and areas of the extracted surface for greater importance is used to provide better overall results. Upon weighting the traces, the cost minimization function is independent of a purely one-to-one alignment error. For example, if weighting is added to some traces or some single points or some areas on the surface of the patient, then the application of a computed transform results in some regions being better aligned to the traces than the rest.

Figure 10:
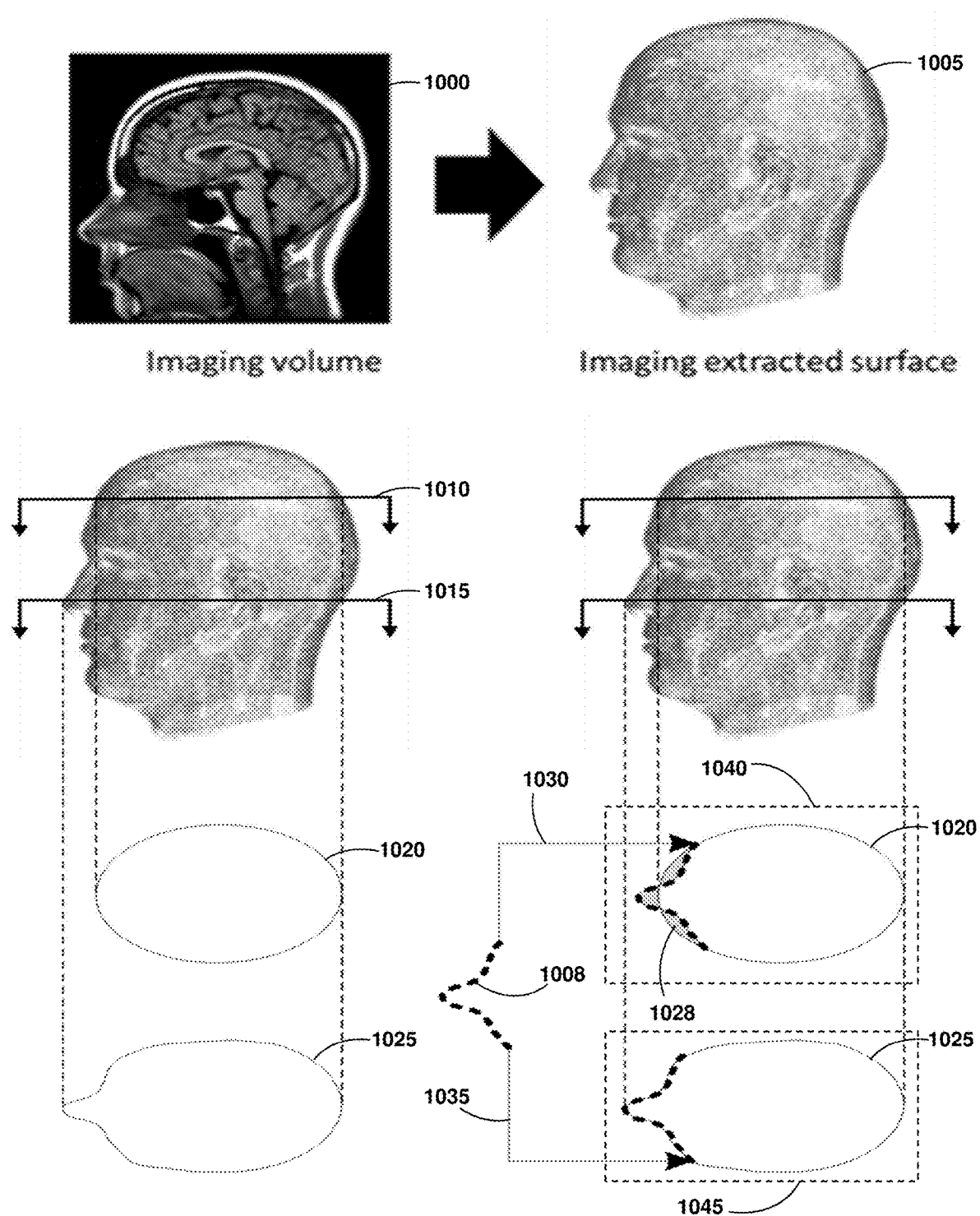
FIG. 10 is a diagram illustrating a transform by the method 601, as shown in FIG. 6, in accordance with an embodiment of the present disclosure.

Referring to FIG. 10, this diagram illustrates a transform by the method 601, as shown in FIG. 6, in accordance with an embodiment of the present disclosure. For example, the computation of a transform from a surface trace 1008 to an extracted surface contour is performed. A patient image 1000 is processed to extract its surface 1005. Two contours 1020 and 1025 of the extracted surface 1005 are also provided for illustrative purposes. A single surface trace 1008 is acquired from the patient that was scanned, such as the patient 707, as shown in FIG. 9. Two transformations 1030 and 1035 are computed and applied to the surface trace 1008. Such transforms are computed by iteratively applying a cost minimization function to the initial surface trace, wherein arguments comprise the sum of spatial deviance 1028 between the surface traces 1008 and the extracted surface of the patient 1005. In one example, the iterative cost minimization function comprises an Iterative Closest Point (ICP) approach to calculate the registration transformation, such as that detailed in "A Method for Registration of 3-D Shapes," by Paul J. Besl and Neil D. McKay, IEEE Transactions on Pattern Analysis and Machine Intelligence, pp. 239-256, VOL. 14, No. 2, February 1992, which is herein, and hereby, incorporated by reference in its entirety. However, any suitable approach is usable, depending on the design criteria of a particular application.

Still referring to FIG. 10, in relation to computing the transform via minimizing the spatial deviances 1028, the iterative computation may, in one iteration, produce the transform 1030 that, when applied to the surface trace 1008, produces the alignment corresponding to frame 1040. While a subsequent iteration may produce the transform 1035 that, when applied to the surface trace 1008, produces the alignment corresponding to frame 1045. The processor then executes the cost minimization function to compare the sum of the deviances for each result 1030 and 1035 and selects the sum of the deviances having the lowest value for the next iteration, and so on, until the deviation value falls below a certain threshold value or meets some alternately defined criteria. Noted is that the term spatial deviances, as used herein, may refer to Euclidean distances between the two sets of points for which the deviance is being calculated.

Referring back to FIG. 6, once step 635 is completed and a transform 910 is derived, the transform 910 is then used to transform any points from the physical coordinate space of the operating room into the image space, thereby effectively coupling the two spaces. Referring back to FIG. 9, this aspect of the patient registration process is illustrated by the physical coordinate space 900 and the image space 915 where the spatial alignments between the patient 707, the patient reference 760, and the pointer tool 702 is duplicated by the virtual representations of these objects in the image space 915, e.g., by the patient scan 706, the virtual patient reference 762, and the virtual pointer tool 714. Noted is that, although the surface contours 906 have been extracted in the image space, in some instances, the surface contours 906 are removed, or made invisible, if desired, thereby reducing visible occlusions of the patient image when a surgeon is operating by using the GUI of the navigation system.

Still referring back to FIG. 6, methods to improve the effectiveness of the computed patient transform for a surface trace patient registration process are implemented, whereby applying the methods of the present disclosure provide better alignment between points on the patient in the physical coordinate space and the extracted surface of the patient image. In some instances, the first of these methods allows the user to modify the acquired surface traces post-acquisition in an attempt to remove any outliers or points that cause the alignment to worsen. In some instances, the second method involves the use of the processor, and through a counting procedure, informs the user of an imbalance in the spatial distribution of points across the different regions of the patient's anatomy. In some instances, the third method involves the aspect of weighting the traces so deviances between some surface traces and the extracted surface of the patient is minimized. In some instances, the fourth method involves the use of combining registration methodologies to produce a better result.

Figure 11:
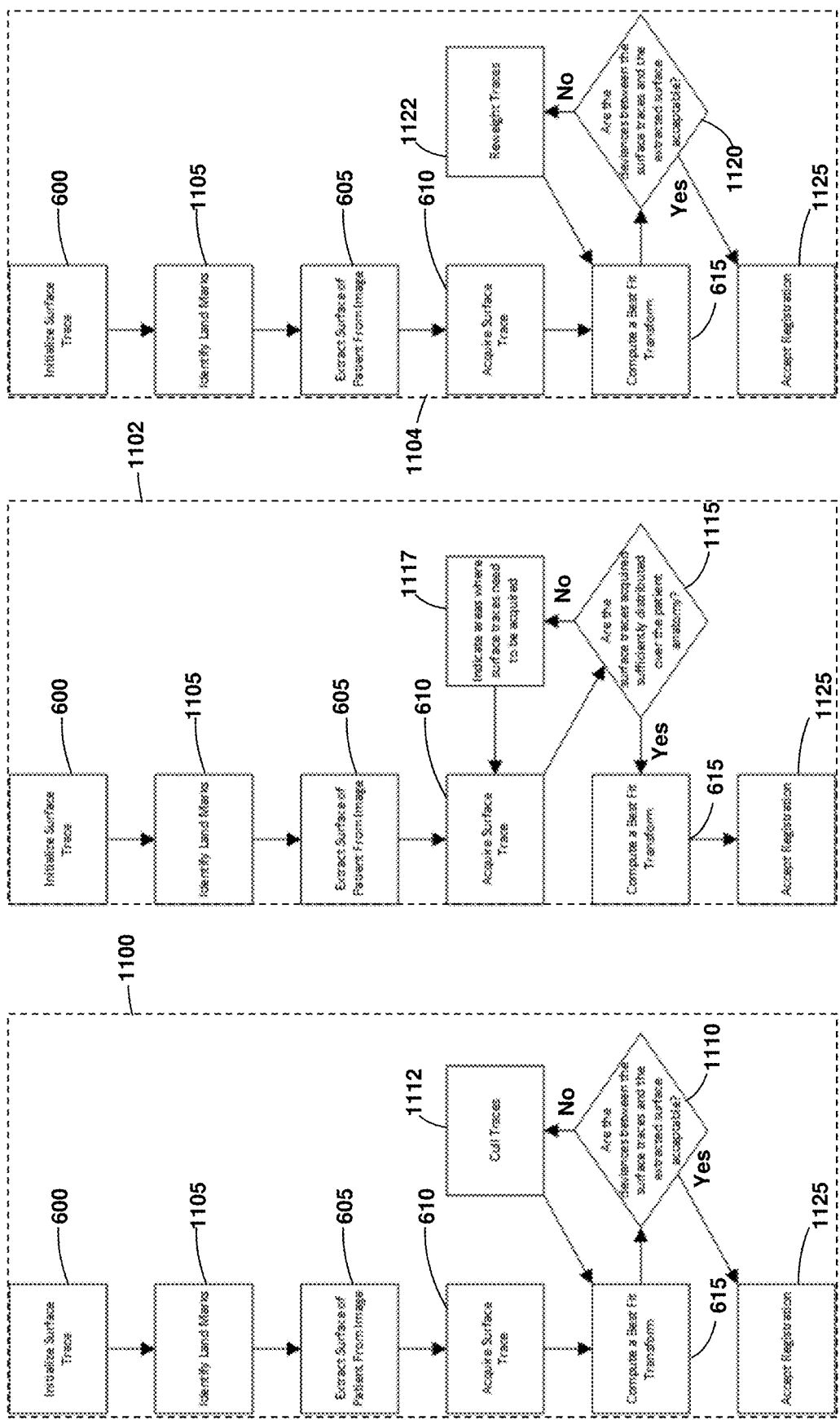
FIG. 11 is a diagram illustrating three flow charts describing further enhancements to the method 601, as shown in FIG. 6, in accordance with an embodiment of the present disclosure.

Referring to FIG. 11, these three flow diagrams illustrate further enhancements to the method 601, as shown in FIG. 6, in accordance with an embodiment of the present disclosure. These three flow diagrams respectively correspond to the first three methods. These flow diagrams illustrate the first three methods, as an augmentation of the surface trace patient registration method, as shown in FIG. 6. More specifically these first three methods incorporate new steps in the surface trace patient registration that improve the outcome of the registration.

Still referring to FIG. 11, the additional step 1105 of identifying landmarks, as performed in each of the methods 1100, 1102, and 1104, streamlines the computation of the transform in the surface trace patient registration process by providing an initial estimate of the patient transform. Providing the initial estimate of the patient transform is performed by identifying at least three points on the patient and deriving a transform similar to the above-described touch point method. Once completed, the outputted registration transform from this step is used as an initial estimate in the first iteration of a computation used to derive a final patient registration transform, such as above-described. For example, the transform outputted by step 1105 is used as an initial estimate in the iterative surface trace method, as described in relation to FIG. 6, or the transform outputted by step 1105 is incorporated with alternate methods, such as those shown in FIG. 11. Since this process is only used to compute an initial estimate of the patient registration transform, unlike the above-described touch point method, the identification of landmark positions, such as the naison, temple, and tip of the nose, among others, need not necessarily be so exact, e.g., the identification of landmarks may not require the use of fiducials. In addition, the corresponding positions of the landmarks on the patient image is manually identified by the user or automatically determined by the processor.

Still referring to FIG. 11, the first flow chart 1100 illustrates the manner in which the computed transform is used for improving patient registration via the culling of surface traces that have been acquired in step 610 of the surface trace registration process. The additional loop of culling the traces follows the computation step 615 and involves the decision step 1110 and the action step 1112. The decision step 1110 requires the user, or in alternate embodiments, the processor to determine whether the sum of deviations of the one or more surface traces from the extracted surface of the patient image is under a threshold value which is acceptable. If the deviations are acceptable, the patient registration is completed using the computed transform 1125. If the deviations are not acceptable, the surface traces are culled at step 1112, a new transform is computed at step 615, and the loop repeats until a transform which produces an acceptable amount of deviances is found.

Figure 12:
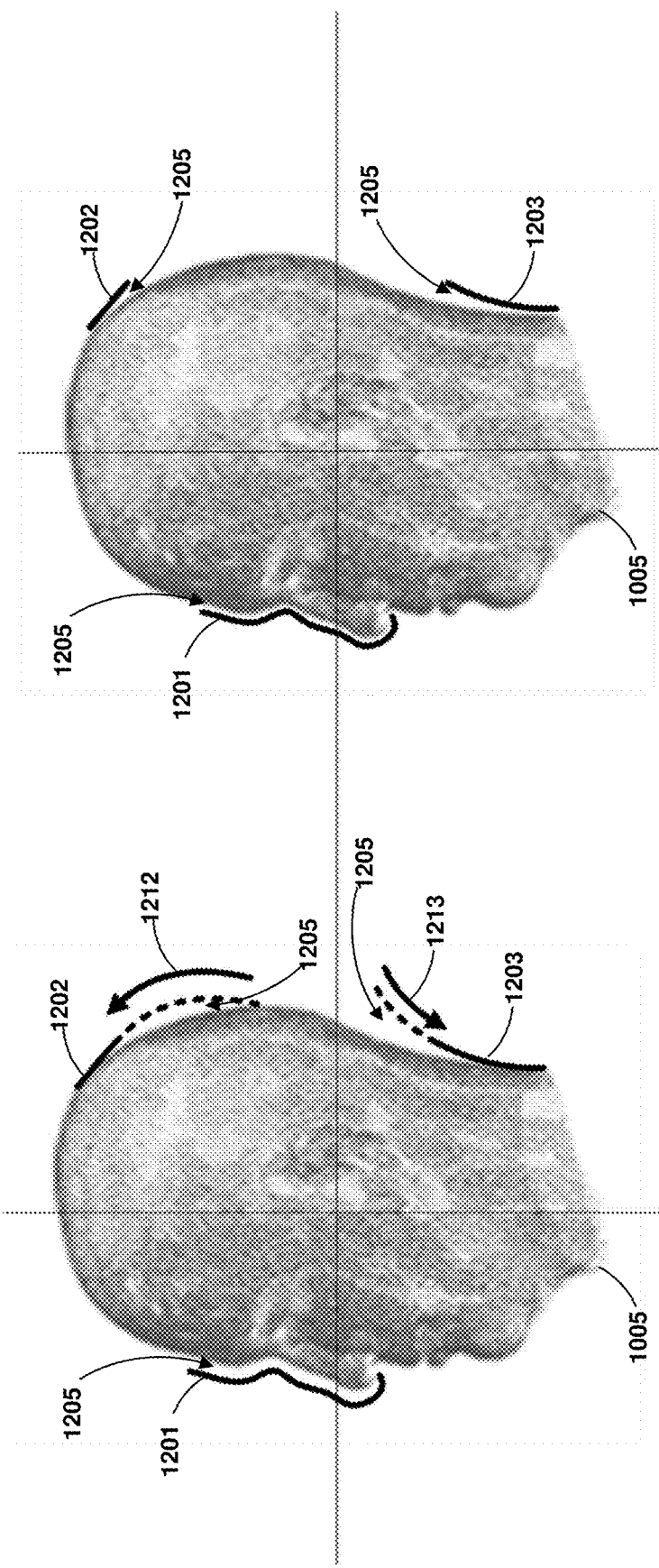
FIG. 12 is a diagram illustrating the effect of the first enhancement, as shown in FIG. 11, in accordance with an embodiment of the present disclosure.

Referring to FIG. 12, this diagram illustrates the effect of the first enhancement, as shown in FIG. 11, in accordance with an embodiment of the present disclosure. An example implementation of the culling step 1112 is shown. The left side of FIG. 12 shows an extracted surface from a patient image 1005 overlaid with transformed surface traces 1201, 1202, and 1203 before any of the traces have been culled. A significant deviation between the extracted surface 1005 and the surface traces at areas 1205 exists. This significant deviation is caused by many factors, such as human error, e.g., the pointer tool tip being removed from the surface of the patient at the end of a surface trace, practical limitations relating to the image space having a limited resolution, the accuracy of the tracking system in converting coordinates from the physical coordinate space to the image space, or any other sources of error that may have affected the patient registration. Nonetheless, one way to account for some of this error, such as the accidental lifting of the tool from the patient, is culling the trace over that region.

Still referring to FIG. 12, for example, given that the tail end (dashed segment) of surface trace 1203 is acquired when the pointer tool is removed from the surface of the patient, then culling the surface trace at that region, for example, as indicated by arrow 1213, reduces the minimum deviation of the optimal transform that is computable by the processor of the navigation system. In addition, in areas of the head having hair (not visible on patient image) a surface trace may have many regions of inaccurate points for at least that the hair occludes the surfaces needed to be acquired and accurately traced. For example, given such was the case for the tail end of surface trace 1202, then removing (culling) this area, as indicated by arrow 1212, reduces the minimum deviation of the optimal transform computable by the processor of the navigation system. On the right side of FIG. 12, the fit results of the surface traces after the culling of the two traces 1212, and 1213 have been applied. After the culling, the fit of the surface traces is better and, more specifically, the deviations in areas 1205 of the right side of FIG. 12 are reduced.

Referring back to FIG. 11, the second flow diagram 1102 illustrates the manner in which the computed transform is used for improving patient registration via increasing the spatial coverage of the surface traces acquired in step 610 of the surface trace registration process. The additional loop of assuring sufficient spatial coverage of the surface traces follows the surface trace acquisition step 610 and involves the decision step 1115 and the action step 1117. The decision step 1115 requires the user or in alternate embodiments the processor to determine whether the spatial distribution of points derived from the surface traces are sufficiently distributed over the patient anatomy. If the deviations are acceptable then the patient registration is completed using the computed transform 1125. If the deviations are not acceptable then the processor indicates areas on the patient image 1117 where further surface traces are needed. The process then returns to the acquire surface trace stage 610 and the loop is repeated until the system captures enough surface traces to assure sufficient coverage of the patient image.

Figure 13:
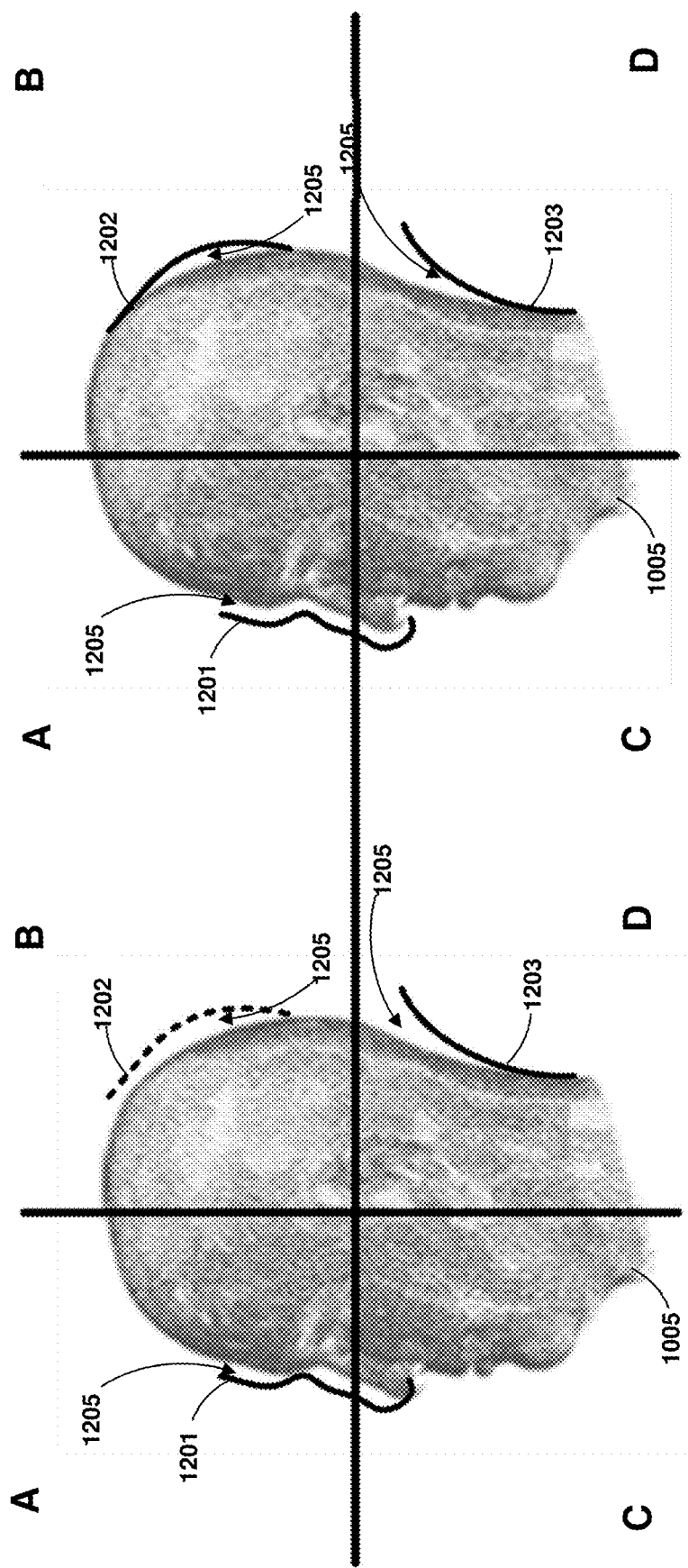
FIG. 13 is a diagram illustrating the effect of the second enhancement, as shown in FIG. 11, in accordance with an embodiment of the present disclosure.

Referring to FIG. 13, this diagram illustrates the effect of the second enhancement, as shown in FIG. 11, in accordance with an embodiment of the present disclosure. The distribution of the surface traces over the patient anatomy is shown. The left side of FIG. 13 shows an extracted surface from a patient image 1005 overlaid with transformed surface traces 1201, 1202, and 1203 before trace 1202 has been acquired by the processor (hence why it's dashed). A significant deviation between the extracted surface 1005 and the surface traces at areas 1205 exists. This significant deviation is caused by many factors, such as the above-described factors. The fit of the acquired surface traces to the data is more vertically deviated than horizontally deviated; and this circumstance is perceivable when observing the nose alignment with the trace 1201. A source of this deviation may arise from insufficiently acquiring points from all the patient's head regions. For example, the acquisition of points tends to be middle-heavy to bottom-heavy and balanced between the left and right. Thus, the fit of the trace tends toward the upper areas of the scan. As above-indicated, one technique for addressing this shortcoming comprises: identifying, to the user, that a sufficient number of points have not been acquired points to be sufficiently distributed on the patient's anatomy; and prompting the user, or the processor of the navigation system, to execute scanning further distributed traces.

Still referring to FIG. 13, for example, the processor may segment the patient image into regions A, B, C, and D. Then, from the left side of FIG. 13, the surface traces 1201 and 1203 cover quadrant regions A, D, and C, of the patient image, but the surface traces 1201 and 1203 do not cover the quadrant B. Thus, in step 1117, the system may indicate, to the user, that the user, or the processor of the navigation system, should acquire a surface trace in that region, e.g., the region B. After subsequently acquiring a surface trace, such as trace 1202, and recalculating the patient registration transform, the right side of FIG. 13 shows that the alignment of the patient image with the surface traces is now more vertically balanced. Moreover, the identification of regions of the patient where more traces should be acquired via step 1117 is determined using additional metrics other than the above-described spatial distribution. For example, traces, acquired from regions of the patient having more pronounced features, are generally more useful in computing a transform than their more uniform counterparts, as such traces tend to have less redundant geometries than other parts of the patient surfaces. To illustrate, when acquiring a surface trace of a patient head, the face, in comparison to the left side of the head, tends to have more unique geometries than the right side of the head, in comparison to the left side of the head, or the top, in comparison to the back of the head. Thus, when determining which regions require more coverage to prompt the user for acquisition, the navigation system processor may suggest areas based on the amount of unique features, rather than only the distribution of surface traces on the image. Accordingly, in some instances, the anatomical areas of the patient image are used to define the regions that are used to determine the spatial distribution of traces over the patient.

Referring back to FIG. 11, the third flow chart 1104 describes how the computed transform is used for improving patient registration via weighting surface traces that are acquired in step 610 of the surface trace registration process. The term weighting, as above-described, refers to prorating the values of a particular surface trace when being used to compute the transform; and, in some instances, prorating the values comprises normalizing a set of constants reflective of the relative ranking of each of the traces relative to one another. The additional loop of weighting the surface traces follows the computation step 615 and comprises the decision step 1120 and the action step 1122. The decision step 1120 requires the user or in alternate embodiments the processor to determine whether the sum of deviations of the one or more surface traces from the extracted surface of the patient image is under a threshold value which is acceptable. If the deviations are acceptable then the patient registration is completed and the transform 1125 computed. If the deviations are not acceptable then the surface traces are reweighted at step 1122, a new transform is computed at step 615; and the loop repeats until a transform which produces an acceptable amount of deviances is found.

Figure 14:
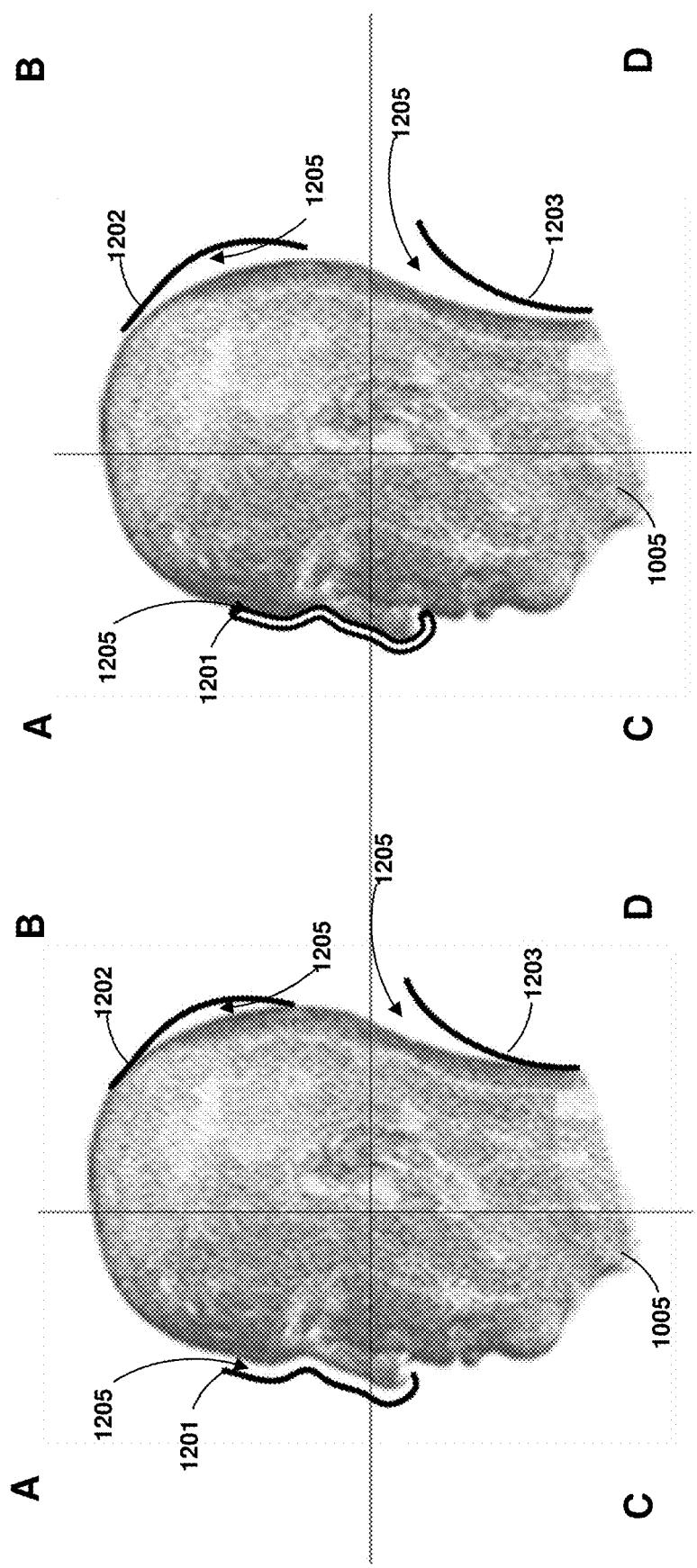
FIG. 14 is a diagram illustrating the effect of the third enhancement, as shown in FIG. 11, in accordance with an embodiment of the present disclosure.

Referring to FIG. 14, this diagram illustrates the effect of the third enhancement, as shown in FIG. 11, in accordance with an embodiment of the present disclosure. For example, the effects of applying a greater weight to a surface trace on the computed transform are shown. The left side of FIG. 14 shows an extracted surface from a patient image 1005 overlaid with transformed surface traces 1201, 1202, and 1203 before any of the traces are ranked and weighted. A significant deviation between the extracted surface 1005 and the surface traces at areas 1205 is shown. This significant deviation may result from many factors, such the above-described factors. Nonetheless, one way to account for some of these errors, such as the accidental lifting of the tool from the patient would be to reweight the trace in that region based on a ranking indicative of the traces accuracy or other factors. For example, given that the surface trace 1201 has been acquired without any preventable issues, while the acquisition of the other two surface traces has not proceeded as smoothly, ranking the trace 1201 higher than the other two traces is performed, such that the deviance of each of the points from the surface trace 1201 would be weighted, wherein each would have a greater value than its non-ranked version.

Still referring to FIG. 14, for example, given the tail-end of the surface trace 1203 has been acquired when the pointer tool is removed accidentally from the surface of the patient by the user, the surface trace 1202 is acquired by tracing the pointer tool over the occluding hair of the patient; and, consequently, the weighted surface trace 1201 is ranked double the other two traces, wherein each unit of distance that 1201 deviates from the extracted surface 1005 would be worth double of each unit of distance than either of the other two surface traces deviates from the extracted surface 1005. Thus, the right side of FIG. 14 shows that the weighted surface trace 1201 (shown as a double line to indicate the weighting) has more of an impact on the transform as per its greater influence for at least its greater weight. The surface trace 1201 also resultantly influences the patient registration transform by orienting the extracted surface further into the left quadrants A and C as compared to their counterpart traces on the left side of FIG. 14 with no weighting.

Still referring to FIG. 14, in alternate implementations of the system and methods described herein, the weighting factors, as described above, are applied to individual segments that make up a trace as opposed to the trace itself. For example, if a surface trace comprises a plurality of points, then the system, as described herein, allows the user to weigh individual points or groups of points at different ranks, thereby potentially magnifying the capacity of the user to attain the best patient registration. In another implementation, the user may select points or groups of points via the same process in which a trace is culled as described above. In some embodiments, a slider is used to indicate the segments of a surface trace (points, vector, amongst other constituent structures) to be culled or reweighted and a GUI may enable a user to indicate a weighting for those sections. In other embodiments, the slider is replaced by a switch in the form of a knob similar to a dimmer switch, or a text box allowing for an input such that the user may input an index referring to the sections to be reweighted or culled and their weights, the GUI may also allow the user to visually select or outline segments of the trace to be reweighted or culled using for example a cursor controlled by a mouse, and any other embodiments such that the user is able to identify the segment of the surface trace to be culled or reweighted. In this implementation, choosing a segment of a surface trace and subsequently assigning it a weight of 0 would affect the registration transform in effectively the same way as culling the same segment in the method described above.

Still referring to FIG. 14 and referring back to FIG. 12, in an additional implementation of the system and methods, described herein, the surface traces are weighted based on an estimation of the quality of their acquisition. For example, in the process 1104, the step of reweighting the trace 1122 in the context of trace 1203 need not be applied broadly to the entire trace 1203. Rather, the step of reweighting the trace 1122 could be segmented, such that only the deviating portion of the tail-end 1213 would receive a lower weight, while the non-highlighted segment would retain its original weight.

Still referring to FIG. 14 and referring back to FIG. 12, yet another implementation the unique weighting of the traces (or constituent structures) is based on their effectiveness in computing the registration based on computational metrics. For example, traces that are acquired from regions of the patient having more pronounced features are more useful in computing a transform compared to their more uniform counterparts as they tend to have less redundant geometries than other parts of the patient surfaces. To illustrate, when acquiring a surface trace of a patient head, the face in comparison to the left side of the head tends to have more unique geometries than the right side in comparison to the left side of the head or the top and the back of the head. Having an area with these less redundant features, thus, has a lower probability of an inaccurate registration. Moreover, another metric that is considered would be the density of points per volume of traces. For example, a trace that has a 100 points covering an area of 5 $mm^2$ has many redundant points compared to a trace with 50 points covering an area of 5 $cm^2$. Thus, weighting the second trace higher than the first will likely lead to the computation of a more accurate transform. Examples of weighting traces and their constituent structures, as described above, exemplify the system and methods, as described herein, and should not be construed to limit the subject matter of the present disclosure.

Still referring to FIG. 14 and referring back to FIGS. 3 and 11, in some instances, the methods mentioned above are implemented by the surgical navigation system (FIG. 3). More specifically, any interaction between the user and the system is performed through the use of the user interface 372 through a display, e.g., as depicted in FIG. 2, and with medical instruments, such as instrument 360. Further, any of the steps requiring analysis of the deviance of the surface traces and the extracted surface from the patient is displayed to the user for providing information regarding the processes being executed, e.g., while acquiring surface traces after the initial estimate of the registration transform is calculated via step 1105 (FIG. 11).

Figure 15:
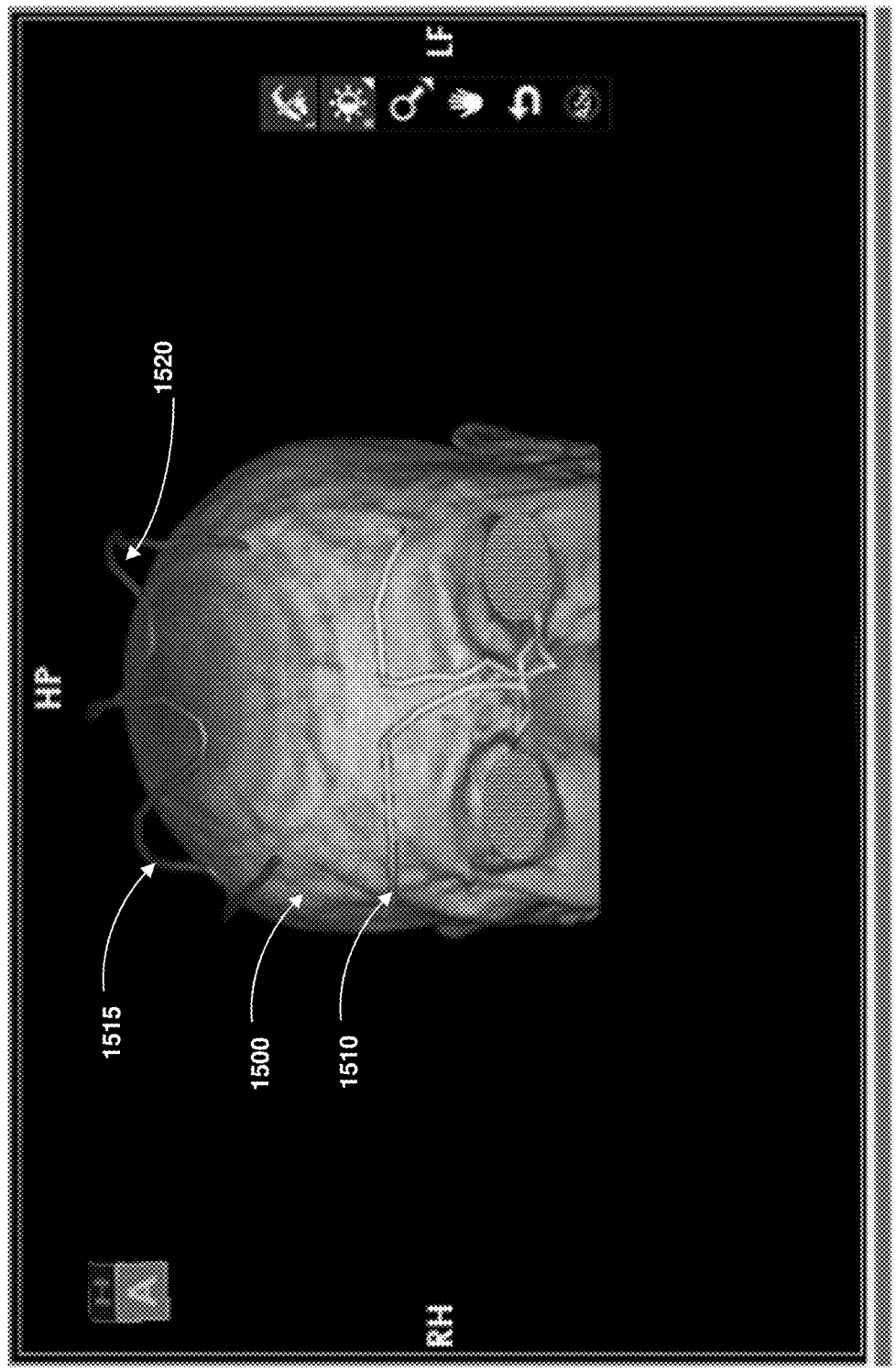
FIG. 15 is a diagram illustrating a display showing a number of surface traces acquired after an initial alignment is provided for patient registration, in accordance with an embodiment of the present disclosure.

Referring to FIG. 15 and referring back to FIG. 4, this diagram illustrates a display showing a number of surface traces acquired after an initial alignment is provided for patient registration, in accordance with an embodiment of the present disclosure. For example, a GUI showing two traces 1515 and 1510, visible atop an extracted patient surface 1500, is used to determine whether the transform provides a sufficient accuracy or requires a refinement using one of the methods described herein. For example, the gap between the surface trace 1515 and the extracted surface of the patient 1500, indicated by 1520, may provide the user with enough information to inform the user that a refinement is needed. In addition, in certain situations, the trace may intersect the surface (not shown) which is also indicative of an inaccurate transform for the patient registration. Thus, a user interface is implemented to the benefit of the user in providing them real-time feed-back of the alignment of the surface traces with regards to the extracted surface of the patient during acquisition of the traces. This feature streamlines the process of patient registration, rather than completing the patient registration step, and subsequently confirming the alignment, such as in the step 412 (FIG. 4), only to have to return to the previous step 406 of initiating the registration and completing the entire registration process again.

Still referring to FIG. 15 and referring back to FIG. 6, in some instances, a method that is used to improve the patient registration process involves using the touch-point registration, as described above, in combination with the surface trace registration, as described herein. In this additional method, touch points are added into the computation and reduce the deviance between the surface trace points and the extracted surface of the patient image, thereby resulting in a better outcome. While in other embodiments, such as during the computation of a patient-registration using the touch-point method, described above, an embodiment, as shown as 621 (FIG. 6), the surface trace is used to supplement missing touch-points or add more information that could be used to refine the patient registration and provide a better patient registration transform.

Figure 16:
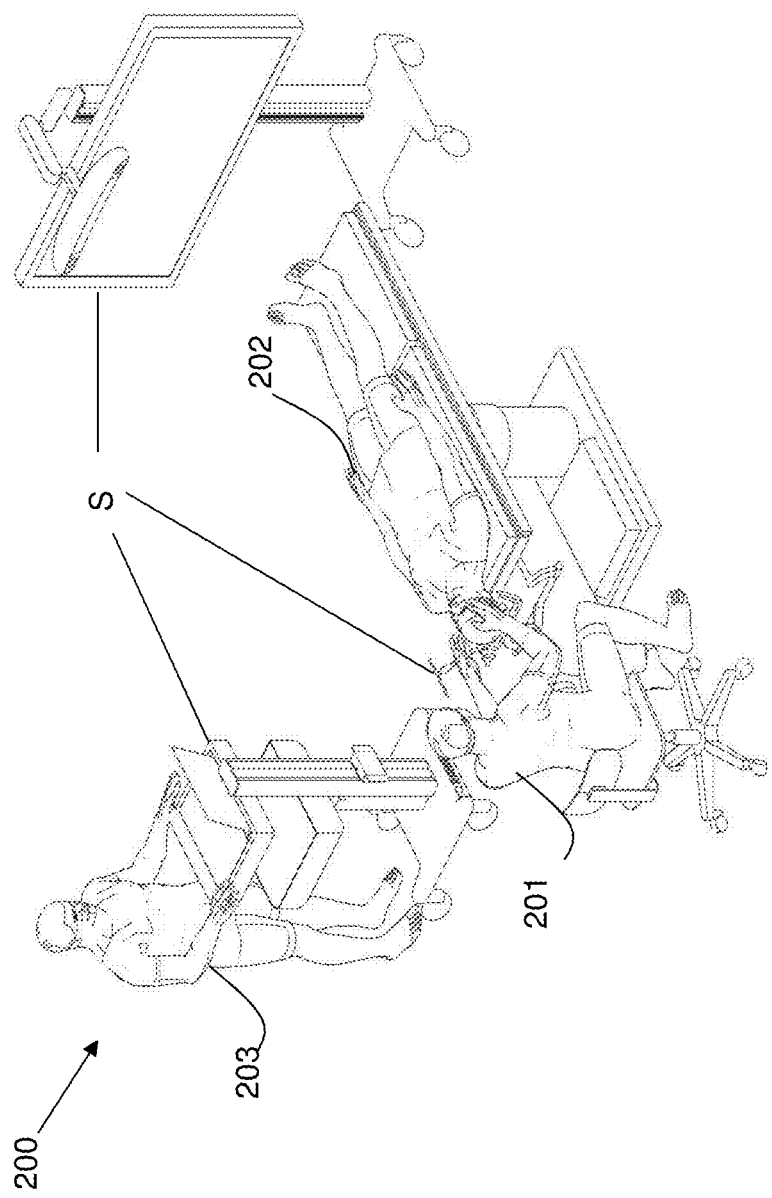
FIG. 16 is a diagram illustrating a surgical navigation system, usable for navigated surgical procedures, in accordance with an embodiment of the present disclosure.

Referring to FIG. 16, this diagram illustrates a medical or surgical navigation system S. usable for navigated surgical procedures, in accordance with an embodiment of the present disclosure. By example only, the medical or surgical navigation system S supports minimally invasive access port-based surgery and is shown in an exemplary navigation system environment 200. The medical or surgical navigation system S is usable for supporting navigated image-guided surgery. For example, a surgeon 201 performs surgery on a patient 202 in an operating room (OR) environment.

Still referring to FIG. 16, the medical or surgical navigation system S comprises: a tracked pointer tool, such as the tracked pointer tool 702, for identifying positions on the patient 202; a tracking system, such as the tracking system 321, for tracking the pointer tool; at least one processor, such as the processors 302, programmed with instructions, such as set of executable instructions, to: initialize a surface trace acquisition; continuously record the positions of the pointer tool during the surface; trace acquisition; combine the positions recorded during the surface trace acquisition into a surface trace; receive a patient image of the patient; extract a surface from the patient image; compute a registration transform between the one or more surface traces and the surface for patient registration, the patient registration dynamically updated during the surface trace acquisition, such as during performance of step 422; segment the patient image into a plurality of regions, each region of the plurality of regions containing an anatomical landmark; determine a spatial distribution of surface traces among the plurality of regions; determine whether the spatial distribution in relation to each region of the plurality of regions minimizes deviance below a threshold; and, if the spatial distribution in relation to any region of the plurality of regions is determined as exceeding the threshold, provide information relating to such region, in accordance with an embodiment of the present disclosure.

Still referring to FIG. 16, the medical or surgical navigation system S further comprises: an equipment tower, a tracking system, at least one display, e.g., displays, and tracked instruments for assisting the surgeon 201 during a medical procedure, such as a surgery, in accordance with an embodiment of the present disclosure. An operator 203 is also present to operate, control, and provide assistance for the medical or surgical navigation system S.

Still referring to FIG. 16, in the system S, the instruction to compute a registration transform comprises an instruction to minimize a set of Euclidean distances. The instruction to compute a registration transform comprises an instruction to iteratively input registration transforms into a cost minimization function. The processor is programmed with further instruction to: initialize a fiducial position acquisition; record the position of the pointer tool during the fiducial position acquisition; and receive the location of fiducials points in the patient image. The processor is programmed with further instructions to: monitor the position of the pointer tool with the tracking system by recording the pointer tool positions; analyze the pointer tool positions to determine if the pointer tool is motionless; and upon determining that the pointer tool is motionless for a predetermined amount of time, prompt the processor to initialize the surface trace acquisition.

Still referring to FIG. 16, in the system S, the instruction to compute a registration transform further comprises: an instruction to receive input, from a user, ranking the one or more surface traces; an instruction to compute a weighting for the surface traces based on the ranking; an instruction to apply the weighting to the surface traces; and an instruction to compute a registration transform that minimizes a set of Euclidean distances between the one or more surface traces and the surface. The instruction to compute a registration transform further comprises: an instruction to receive input from a user of one or more regions of one or more surface traces to be culled; an instruction to discard the one or more regions from the one or more surface traces; and an instruction to compute a registration transform that minimizes a set of Euclidean distances between the one or more surface traces and the surface after the regions have been discarded.

Still referring to FIG. 16, the system S further comprises a display having a GUI for receiving input from a user. The instruction to compute a registration transform further comprises: an instruction to initialize one or more landmark acquisitions; an instruction to record the positions of one or more landmarks on a patient; an instruction to receive the position of one or more landmark points in the patient image; and an instruction to compute an initial registration transform that minimizes a set of Euclidean distances between the one or more landmarks and the one or more landmark points. The processor is programmed with further instructions to use the initial registration transform to visualize, on the display, an initial alignment of the patient's position with the patient image in an image space.

Still referring to FIG. 16, in the system S, the processor is programmed with an instruction to: dynamically update the patient registration in real time during a surface trace acquisition; and to provide visual feedback, e.g., via a display. The instruction to update the patient registration in real time during a surface trace acquisition comprises an instruction to iteratively apply a new registration corresponding to a set of newly collected points to the patient registration, thereby refining the patient registration, thereby updating a set of positions corresponding to the set of newly collected points, and thereby improving the patient registration. The dynamic registration updates facilitate the surgeon's understanding as to the manner in which surface trace acquisition affects registration, thereby providing direct training feedback.

Still referring to FIG. 16, in the system S, the processor is programmed with an instruction to improve landmark registration, e.g., at initialization of a surface trace acquisition, by registering a deformative registries to a template, rather than performing a linear affine registration. In order to identify the orientation of any arbitrary scan, the processor is programmed with an instruction to perform a deformative registration to a template with a known orientation. This deformative registration has much more degrees of freedom, e.g., greater than 12 degrees of freedom, in relation to affine registration having 12 degrees of freedom, whereby a better fit to the template head shape is provided, and whereby landmark registration is improved, e.g., in a range of approximately 0 mm to approximately 15 mm. The parameters for executing the instruction to improve landmark registration are tunable, wherein thereof comprises a duration in a range of up to approximately a duration of performing a linear registration. " . . . The instruction to improve landmark registration further comprises an instruction to apply a set of landmark points, e.g., 3 initial points to 5 initial points, for guiding an initial registration. An instruction comprising an algorithm will then be applied to calculate the rigid transformation which minimizes the average squared distance between captured landmark points and the corresponding points in the patient image. Using deformative registration to align the template with the patient image improves the positional accuracy of the anatomical landmark points in the patient image, thereby improving landmark registration, and thereby providing a better initial guess for executing an instruction comprising a surface trace registration algorithm.

Still referring to FIG. 16, in the system S, in general, improving the initial registration has at least the following beneficial impacts: (a) a subsequent surface trace registration is faster and more accurate than in related art registrations; and (b) a better visual feedback as well as more accurate template-based coverage metric are provided for at least that the better initial guess is closer to a final result. In addition, in the system S, improved template-based coverage metrics are provided by at least the following techniques: (a) computing the coverage extent of each region, rather than merely counting the number of points in each region; (b) applying different weights corresponding to different points based on complexity of an underlying surface, e.g., by determining size of the corresponding mesh faces; and (c) applying different weights corresponding to different regions based on a degree to which the different corresponding regions impact registration accuracy.

Figure 17:
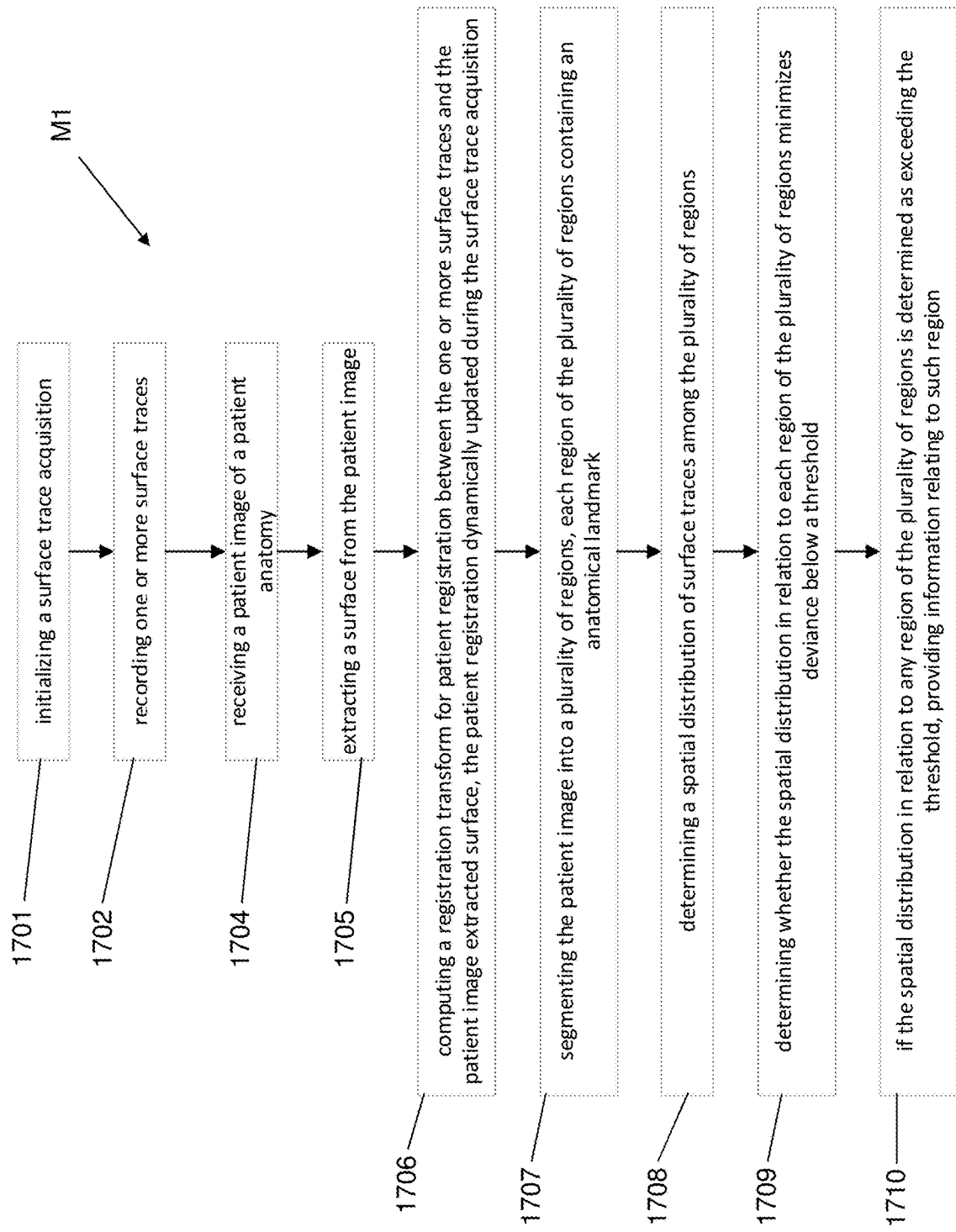
FIG. 17 is a flow diagram illustrating a method of performing a patient registration using a surgical navigation system, in accordance with an embodiment of the present disclosure.

Referring to FIG. 17, this flow diagram illustrates a method M1 of performing a patient registration using a surgical navigation system, having a processor, in a medical procedure, the method M1 comprising: initializing a surface trace acquisition, as indicated by block 1701; recording one or more surface traces, as indicated by block 1702; receiving a patient image of a patient anatomy, as indicated by block 1704; extracting a surface from the patient image, as indicated by block 1705; computing a registration transform for patient registration between the one or more surface traces and the patient image extracted surface, the patient registration dynamically updated during the surface trace acquisition, as indicated by block 1706; segmenting the patient image into a plurality of regions, each region of the plurality of regions containing an anatomical landmark, as indicated by block 1707; determining a spatial distribution of surface traces among the plurality of regions, as indicated by block 1708; determining whether the spatial distribution in relation to each region of the plurality of regions minimizes deviance below a threshold, as indicated by block 1709; and if the spatial distribution in relation to any region of the plurality of regions is determined as exceeding the threshold, providing information relating to such region, as indicated by block 1710, in accordance with an embodiment of the present disclosure.

Still referring to FIG. 17, in the method M1, computing a registration transform comprises minimizing a set of Euclidean distances. Computing a registration transform comprises iteratively inputting registration transforms into a cost minimization function. The method M further comprises: initializing a fiducial position acquisition; recording the positions of fiducials on the patient; and receiving the location of fiducials points in the patient image. The method M1 further comprises: monitoring the position of a pointer tool; analyzing the position to determine if the pointer tool is motionless; and upon determining that the pointer tool is motionless for a predetermined amount of time, prompting the surgical navigation system to initialize or optionally terminate the surface trace.

Still referring to FIG. 17, in the method M1, computing a registration transform further comprises: receiving input from a user ranking the one or more surface traces; computing a weighting for the surface traces based on the ranking; applying the weighting to the surface traces; and computing a registration transform that minimizes a set of Euclidean distances between the one or more surface traces and the surface. Computing a registration transform further comprises: receiving input from a user of one or more regions of one or more surface traces to be culled; discarding the one or more regions from the one or more surface traces; and computing a registration transform that minimizes a set of Euclidean distances between the one or more surface traces and the surface after the regions have been discarded.

Still referring to FIG. 17, in the method M1, computing a registration transform further comprises: initializing one or more landmark acquisitions; recording the positions of one or more landmarks on a patient; receiving the position of one or more landmark points in the patient image; and computing an initial registration transform that minimizes a set of Euclidean distances between the one or more landmarks and the one or more landmark points. The method M1 further comprises using the initial registration transform to visualize an initial alignment of the patient's position with the patient image in an image space. The method of M1 further comprises visualizing the surface traces in the image space.

Figure 18:
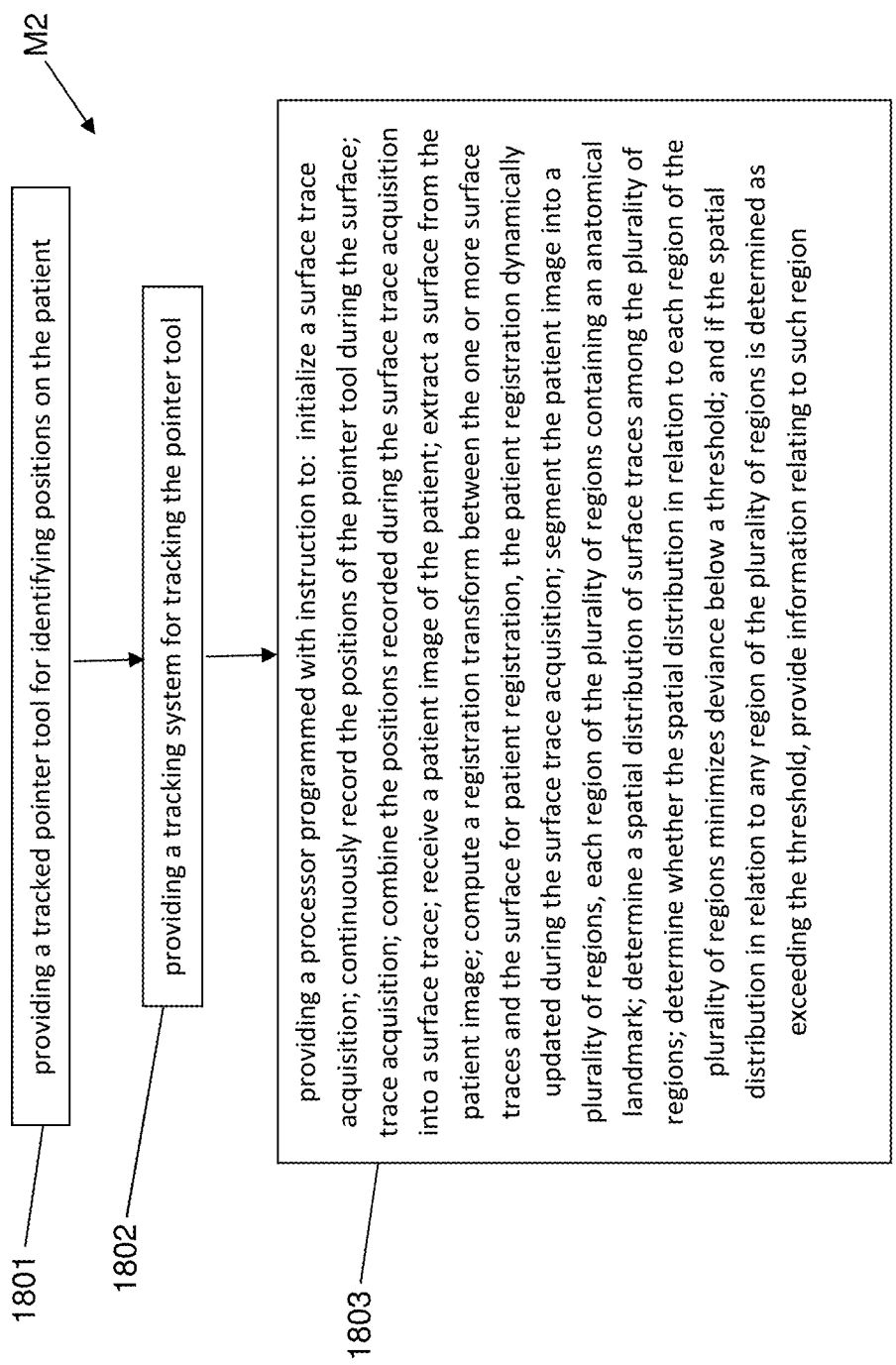
FIG. 18 is a flow diagram illustrating a method of fabricating a surgical navigation system, usable for navigated surgical procedures, in accordance with an embodiment of the present disclosure.

Referring to FIG. 18, this flow diagram illustrates a method M2 of fabricating a surgical navigation system S, usable for navigated surgical procedures, the method M2 comprising: providing a tracked pointer tool for identifying positions on the patient, as indicated by block 1801; providing a tracking system for tracking the pointer tool, as indicated by block 1802; and providing a processor programmed with instruction to: initialize a surface trace acquisition; continuously record the positions of the pointer tool during the surface; trace acquisition; combine the positions recorded during the surface trace acquisition into a surface trace; receive a patient image of the patient; extract a surface from the patient image; compute a registration transform between the one or more surface traces and the surface for patient registration, the patient registration dynamically updated during the surface trace acquisition; segment the patient image into a plurality of regions, each region of the plurality of regions containing an anatomical landmark; determine a spatial distribution of surface traces among the plurality of regions; determine whether the spatial distribution in relation to each region of the plurality of regions minimizes deviance below a threshold; and if the spatial distribution in relation to any region of the plurality of regions is determined as exceeding the threshold, provide information relating to such region, as indicated by block 1803, in accordance with an embodiment of the present disclosure.

Figure 19:
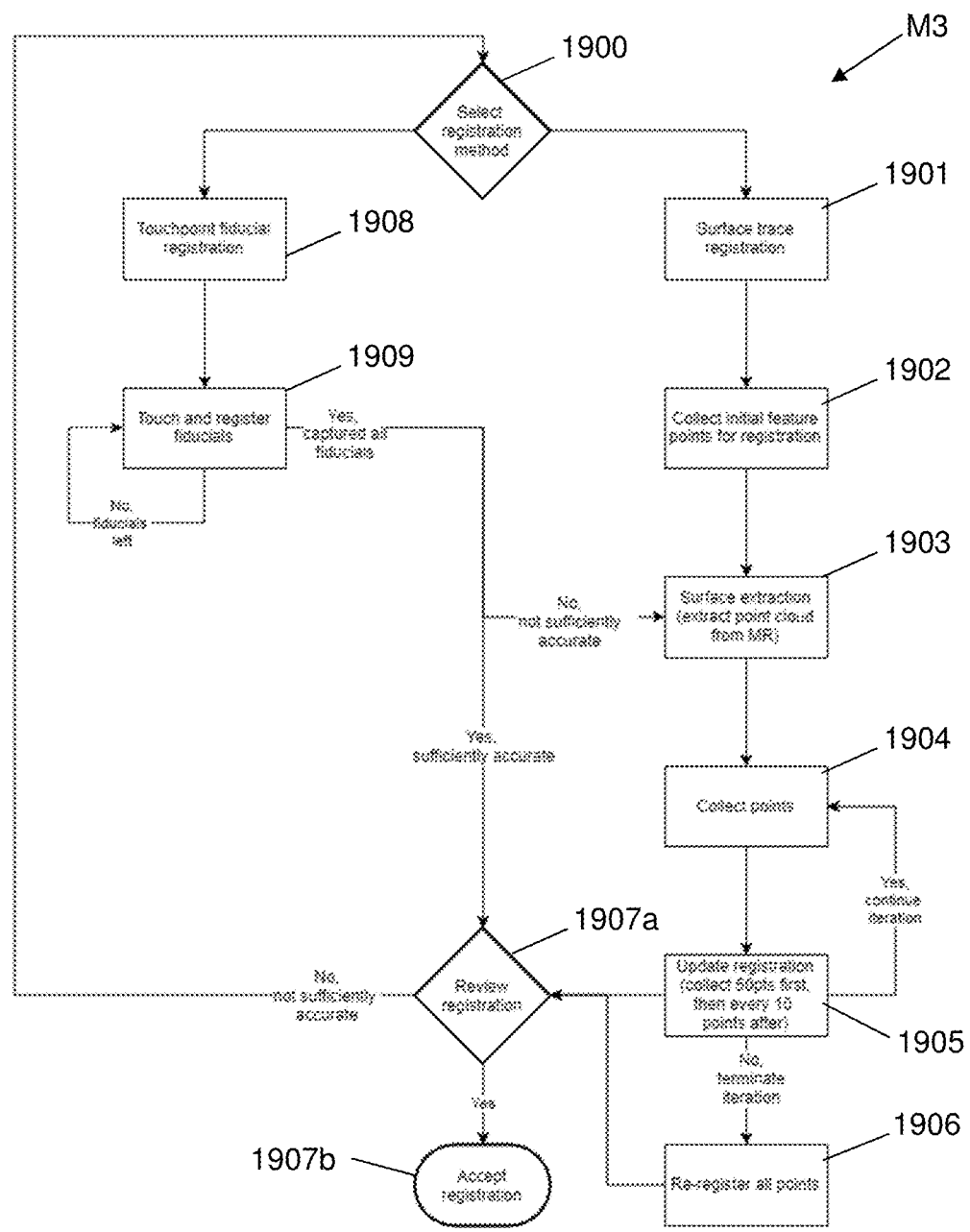
FIG. 19 is a flow diagram illustrating a method of updating a patient registration during surface trace acquisition, in accordance with an embodiment of the present disclosure.

Referring to FIG. 19, this flow diagram illustrating a method M3 of updating a patient registration during surface trace acquisition, in accordance with an embodiment of the present disclosure. The method M3 comprises: selecting a registration technique from a plurality of registration techniques, wherein the plurality of registration techniques comprises a touchpoint fiducial registration technique and a surface trace registration technique, as indicated by block 1900; if the surface trace registration technique is selected, collecting initial feature points, as indicated by block 1901; performing a surface extraction, as indicated by block 1902; collecting initial points, as indicated by block 1903; computing an initial registration by applying a non-linear template-matching technique, thereby providing an initial registration, as indicated by block 1904; updating registration by iteratively collecting points, as indicated by block 1905; and registering all points, thereby providing an updated registration, as indicated by block 1906; if the touchpoint fiducial registration technique is selected, touching and registering a plurality of fiducial points, as indicated by block 1908, and if not sufficiently accurate, repeating touching and registering a plurality of fiducial points, as indicated by block 1909, and, if further refinement is desired, performing a surface extraction, as indicated by block 1903; and reviewing the registration, as indicated by block 1907*a*; and if the registration is determined accurate within a predetermined range, accepting the registration, as indicated by block 1907*b*.

Figure 20:
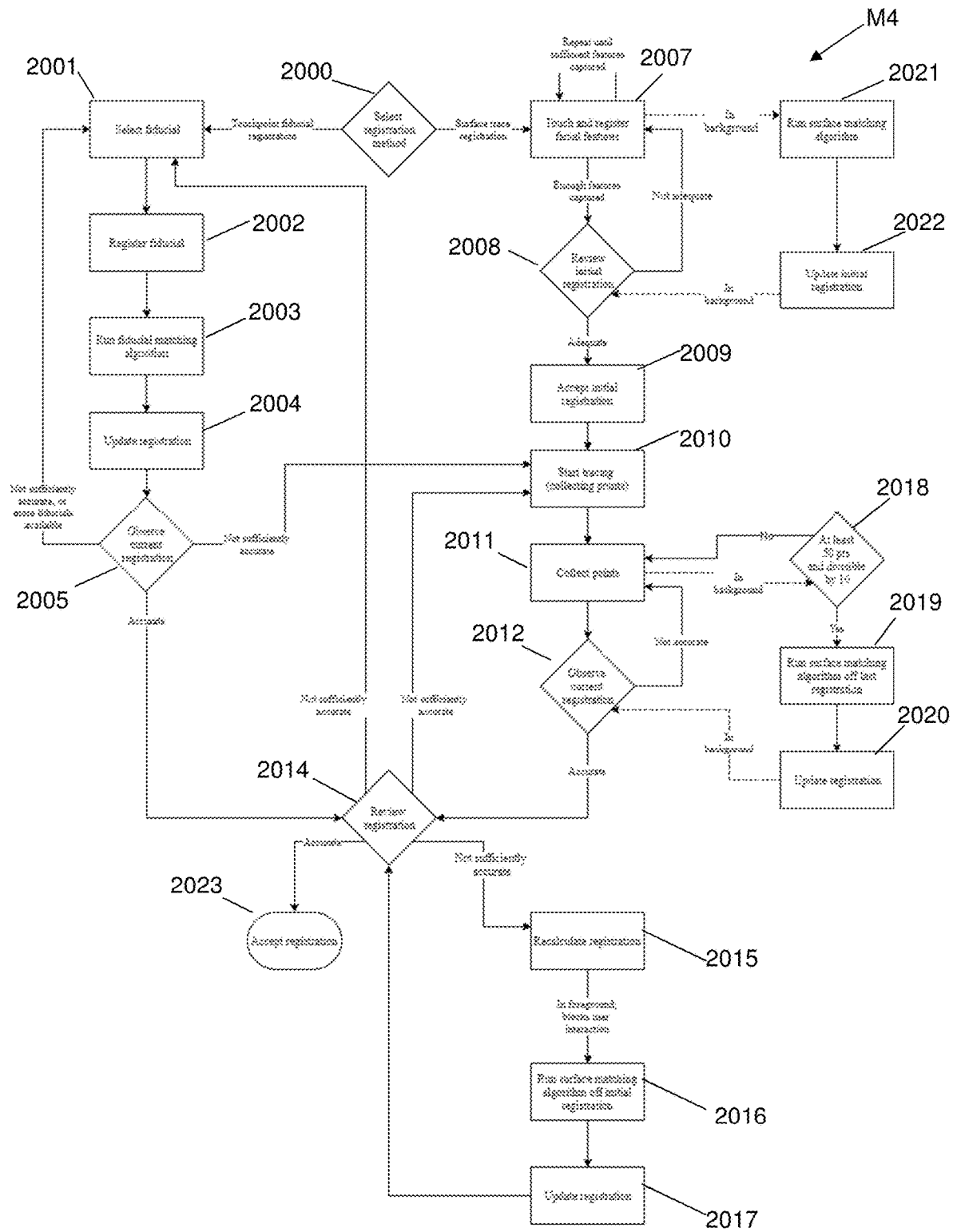
FIG. 20 is a flow diagram illustrating a method of updating a patient registration during surface trace acquisition, operable via at least one of a user interface and a user interaction, in accordance with an alternate embodiment of the present disclosure.

Referring to FIG. 20, this flow diagram illustrating a method M4 of updating a patient registration during surface trace acquisition, operable via at least one of a user interface and a user interaction, in accordance with an alternate embodiment of the present disclosure. The method M4 generally comprises: selecting a registration method or technique, as indicated by block 2000; if a touchpoint fiducial registration technique is selected, selecting a fiducial marker, as indicated by block 2001; and, if a surface-trace technique is selected, iteratively touching and registering a plurality of facial features until a sufficient number of facial features are captured, as indicated by block 2007, in accordance with an alternate embodiment of the present disclosure.

Still referring to FIG. 20, in the method M4, if the touchpoint fiducial registration technique is selected, the following steps are performed: selecting a fiducial marker, as indicated by block 2001; registering the fiducial marker, as indicated by block 2002; running an executable instruction comprising a fiducial-matching algorithm, as indicated by block 2003; updating a current registration, as indicated by block 2004; and observing and determining whether the current registration is sufficiently accurate, such as by being within a predetermined accuracy range, as indicated by block 2005; if the current registration is sufficiently accurate, reviewing and determining whether the current registration is sufficiently accurate, such as by being within a predetermined accuracy range, e.g., as predetermined by the user or in a range of less than approximately 2 degrees, or a range of less than approximately 2 mm, as indicated by block 2014; if the current registration is insufficiently accurate and another fiducial marker is available, selecting a fiducial marker, as indicated by block 2001; and if the current registration is insufficiently accurate and another fiducial marker is unavailable, commencing tracing a surface, such as by collecting points, as indicted by block 2010.

Still referring to FIG. 20, after reviewing and determining whether the current registration is sufficiently accurate, such as by being within a predetermined accuracy range, as indicated by block 2014, the method M4 further comprises: if the current registration is sufficiently accurate, accepting the current registration, as indicated by block 2023; and, if the current registration is insufficiently accurate, performing one of: selecting a fiducial marker, as indicated by block 2001; commencing tracing a surface, such as by collecting points, as indicted by block 2010; and recalculating the current registration, as indicated by block 2015.

Still referring to FIG. 20, after recalculating the current registration, as indicated by block 2015, the method M4 further comprises: in foreground, running an executable instruction comprising a surface-matching algorithm while blocking the user interaction, as indicated by block 2016; updating the current registration, as indicated by block 2017; and reviewing and determining whether the current registration is sufficiently accurate, such as by being within a predetermined accuracy range, as indicated by block 2014.

Still referring to FIG. 20, after commencing tracing a surface, such as by collecting points, as indicted by block 2010, the method M4 further comprises: collecting a plurality of points, as indicated by block 2011; and observing and determining whether the current registration is sufficiently accurate, such as by being within a predetermined accuracy range, as indicated by block 2012; if the current registration is sufficiently accurate, and reviewing and determining whether the current registration is sufficiently accurate, such as by being within a predetermined accuracy range, as indicated by block 2014.

Still referring to FIG. 20, after collecting a plurality of points, as indicated by block 2011, the method M4 further comprises: in background, determining whether a number of collected points exceeds 50 and whether the number of collected points is divisible by 10, as indicated by block 2018; if the number of collected points exceeds 50 and the number of collected points is divisible by 10, running an executable instruction comprising a surface-matching algorithm using an initial registration, as indicated by block 2019; updating the current registration, as indicated by block 2020; and, in background, observing and determining whether the current registration is sufficiently accurate, such as by being within a predetermined accuracy range, as indicated by block 2012; and, if the number of collected points does not exceed 50 and the number of collected points is not divisible by 10, collecting a plurality of points, as indicated by block 2011.

Still referring to FIG. 20, in the method M4, if the surface-trace technique is selected, the following steps are performed: iteratively touching and registering a plurality of facial features until a sufficient number of facial features are captured, such as in relation to at least three regions, e.g., the tip of the nose, the top of the head, the left ear, and the right ear, as indicated by block 2007; if sufficient facial features are captured, reviewing and determining whether the initial registration is adequate, such as by touching the facial features and observing the accuracy, as indicated by block 2008; if the initial registration is adequate, accepting the initial registration, as indicated by block 2009; and commencing tracing a surface, such as by collecting points, as indicted by block 2010; and, if the initial registration is inadequate, iteratively touching and registering a plurality of facial features until a sufficient number of facial features are captured, as indicated by block 2007.

Still referring to FIG. 20, after iteratively touching and registering a plurality of facial features until a sufficient number of facial features are captured, such as in relation to at least three regions, e.g., the tip of the nose, the top of the head, the left ear, and the right ear, as indicated by block 2007, the method M4 further comprises performing the steps of: running an executable instruction comprising a surface-matching algorithm, as indicated by block 2021; in background, updating the initial registration, as indicated by block 2022; and reviewing and determining whether the initial registration is sufficiently accurate, such as by being within a predetermined accuracy range, as indicated by block 2008.

The specific embodiments described above have been shown by way of example, and it should be understood that these embodiments is susceptible to various modifications and alternative forms. It should be further understood that the claims are not intended to be limited to the particular forms disclosed, but rather to cover modifications, equivalents, and alternatives falling within the spirit and scope of this disclosure.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data is stored in various places including for example ROM, volatile RAM, nonvolatile memory and/or cache. Portions of this software and/or data is stored in any one of these storage devices. As used herein, the phrases "computer readable material" and "computer readable storage medium" refers to all computer-readable media, except for a transitory propagating signal per se.

The specific embodiments described above have been shown by way of example, and understood is that these embodiments is susceptible to various modifications and alternative forms. Further understood is that the claims are not intended to be limited to the particular forms disclosed, but rather to cover all modifications, equivalents, and alternatives falling within the spirit and scope of this disclosure.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may appreciated by those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

The present disclosure industrially applies to neurosurgical or medical procedures. More specifically, the present disclosure industrially applies to systems and methods for improving the surface trace patient registration process by using a medical navigation system. Even more specifically, the present disclosure industrially applies to systems and methods for updating patient registration by using a medical navigation system.

What is claimed:

1. A method of dynamically updating a registration real time during a surface trace acquisition, comprising:

selecting a registration technique from a plurality of registration techniques, wherein the plurality of registration techniques comprises a touchpoint fiducial registration technique and a surface trace registration technique;

if the surface trace registration technique is selected,
collecting initial feature points;
performing a surface extraction;
collecting initial points;
computing an initial registration by applying a non-linear template-matching technique, thereby providing an initial registration;
updating registration by iteratively collecting points; and
registering all points, thereby providing an updated registration;
if the touchpoint fiducial registration technique is selected,
touching and registering a plurality of fiducial points and
if not sufficiently accurate, repeating touching and registering a plurality of fiducial points, and
if further accuracy is desired, performing a surface extraction and reviewing the registration; and
if the registration is determined accurate within a predetermined range, accepting the registration.

2. The method of claim 1, if the touchpoint fiducial registration technique is selected, further comprising:
   selecting a fiducial marker;
   registering the fiducial marker;
   running an executable instruction comprising a fiducial-matching algorithm;
   updating a current registration; and
   observing and determining whether the current registration is sufficiently accurate within a predetermined accuracy range;
      if the current registration is sufficiently accurate, reviewing and determining whether the current registration is sufficiently accurate within a predetermined accuracy range;
      if the current registration is insufficiently accurate and another fiducial marker is available, selecting a fiducial marker;
      if the current registration is insufficiently accurate and another fiducial marker is unavailable, commencing tracing a surface;
      if the initial registration is adequate, accepting the initial registration and commencing tracing a surface; and,
      if the initial registration is inadequate, iteratively touching and registering a plurality of facial features until a sufficient number of facial features are captured.

3. The method of claim 2, if the touchpoint fiducial registration technique is selected, further comprising:
   if the current registration is sufficiently accurate, accepting the current registration; and,
   if the current registration is insufficiently accurate, performing one of:
      selecting a fiducial marker;
      commencing tracing a surface, such as by collecting points; and
      recalculating the current registration.

4. The method of claim 2, if the touchpoint fiducial registration technique is selected, further comprising:
   in foreground, running an executable instruction comprising a surface-matching algorithm while blocking the user interaction;
   updating the current registration; and
   reviewing and determining whether the current registration is sufficiently accurate, such as by being within a predetermined accuracy range.

5. The method of claim 2, if the touchpoint fiducial registration technique is selected, further comprising:
   collecting a plurality of points; and
   observing and determining whether the current registration is sufficiently accurate, such as by being within a predetermined accuracy range;
   if the current registration is sufficiently accurate, terminating tracing of the surface, such as by terminating collecting the plurality of points; and
   reviewing and determining whether the current registration is sufficiently accurate, such as by being within a predetermined accuracy range.

6. The method of claim 2, if the touchpoint fiducial registration technique is selected, further comprising:
   in background, determining whether a number of collected points exceeds 50 and whether the number of collected points is divisible by 10;
   if the number of collected points exceeds 50 and the number of collected points is divisible by 10, running an executable instruction comprising a surface-matching algorithm using an initial registration;
   updating the current registration; and,
   in background, observing and determining whether the current registration is sufficiently accurate, such as by being within a predetermined accuracy range; and,
   if the number of collected points does not exceed 50 and the number of collected points is not divisible by 10, collecting a plurality of points.

7. The method of claim 1, if the surface-trace technique is selected, further comprising:
   iteratively touching and registering a plurality of facial features until a sufficient number of facial features are captured;
   if sufficient facial features are captured, reviewing and determining whether the initial registration is adequate;
   if the initial registration is adequate, accepting the initial registration;
   commencing tracing a surface, such as by collecting points; and
   if the initial registration is inadequate, iteratively touching and registering a plurality of facial features until a sufficient number of facial features are captured.

8. The method of claim 1, if the surface-trace technique is selected, further comprising:
   running an executable instruction comprising a surface-matching algorithm;
   in background, updating the initial registration; and
   reviewing and determining whether the initial registration is sufficiently accurate within a predetermined accuracy range.

* * * * *